(12) United States Patent
Labiche

(10) Patent No.: US 12,016,696 B2
(45) Date of Patent: Jun. 25, 2024

(54) DEVICE FOR THE QUALITATIVE EVALUATION OF HUMAN ORGANS

(71) Applicant: SMICES, Le Cres (FR)

(72) Inventor: Clément Labiche, Saint Series (FR)

(73) Assignee: STELLA SURGICAL, Le Cres (FR)

( * ) Notice: Subject to any disclaimer, the term of this patent is extended or adjusted under 35 U.S.C. 154(b) by 0 days.

(21) Appl. No.: 17/467,215

(22) Filed: Sep. 5, 2021

(65) Prior Publication Data
US 2022/0012882 A1     Jan. 13, 2022

Related U.S. Application Data

(63) Continuation-in-part of application No. 16/419,563, filed on May 22, 2019.

(30) Foreign Application Priority Data

Jan. 4, 2019   (FR) ........................................ 1900066
Mar. 4, 2019   (FR) ........................................ 1902202

(51) Int. Cl.
*A61B 5/00*     (2006.01)
*A61B 1/04*     (2006.01)
(Continued)

(52) U.S. Cl.
CPC .............. *A61B 5/4244* (2013.01); *A61B 1/04* (2013.01); *G06T 7/0012* (2013.01); *G06T 7/40* (2013.01);
(Continued)

(58) Field of Classification Search
CPC ......... G06T 7/0012–0016; G06T 2207/10024; G06T 2207/30056; G06T 2207/30092;
(Continued)

(56) References Cited

U.S. PATENT DOCUMENTS 5,827,176 A * 10/1998 Tanaka ..................... A61B 1/05
                                                    600/129
2004/0151379 A1* 8/2004 Kim ....................... A61B 5/416
                                                    382/209
(Continued)

FOREIGN PATENT DOCUMENTS

WO     2017/161097 A1    9/2017

OTHER PUBLICATIONS

Moccia, Sara, Leonardo S. Mattos, Ilaria Patrini, Michela Ruperti, Nicolas Poté, Federica Dondero, Fracçois Cauchy et al. "Computer-assisted liver graft steatosis assessment via learning-based texture analysis." International Journal of Computer Assisted Radiology and Surgery 13 (2018): 1357-1367. (Year: 2018).*

(Continued)

*Primary Examiner* — Edward F Urban
*Assistant Examiner* — Wassim Mahrouka
(74) *Attorney, Agent, or Firm* — Patshegen IP; Moshe Pinchas

(57) ABSTRACT

This method for qualitatively evaluating human livers comprises:
  a step (301) of computing normalized histograms of colour channels from a portion of a photograph of a liver;
  a step (304) of loading coefficients obtained at the end of a training phase;
  a step (305) of extracting from the histograms values corresponding to variables retained at the end of the training phase;
  a step (306) of computing a linear combination of the extracted values weighted with the loaded coefficients; and (Continued)

a step (308, 309) of displaying information representative of the result of the computation of the linear combination.

18 Claims, 13 Drawing Sheets

(51) Int. Cl.
*A61B 1/06* (2006.01)
*G06T 7/00* (2017.01)
*G06T 7/40* (2017.01)
*G06T 7/90* (2017.01)
*G16H 30/40* (2018.01)
*G16H 50/20* (2018.01)

(52) U.S. Cl.
CPC ............... *G06T 7/90* (2017.01); *G16H 30/40* (2018.01); *G16H 50/20* (2018.01); *A61B 1/0661* (2013.01); *G06T 2207/10068* (2013.01); *G06T 2207/20081* (2013.01); *G06T 2207/30056* (2013.01); *G06T 2207/30168* (2013.01)

(58) Field of Classification Search
CPC ....... A61B 5/4244; A61B 5/1032; A61B 1/04; A61B 1/0661; A61B 2505/05; A61B 2505/02; G16H 50/70; G16H 50/40; G16H 50/20; G16H 30/40
USPC .......................................................... 382/128
See application file for complete search history.

(56) References Cited

U.S. PATENT DOCUMENTS

| | | | |
|---|---|---|---|
| 2007/0258625 A1* | 11/2007 | Mirtsching | G16H 20/10 452/155 |
| 2014/0303435 A1* | 10/2014 | Taniguchi | A61B 1/00006 600/103 |
| 2014/0355881 A1* | 12/2014 | Bhardwaj | G06T 5/003 382/173 |
| 2018/0350071 A1* | 12/2018 | Purwar | G06V 10/454 |

OTHER PUBLICATIONS

Rey, J. W., et al. "Hepatic steatosis in organ donors: disparity between surgery and histology?." Transplantation proceedings. vol. 41. No. 6. Elsevier, 2009. (Year: 2009).*

"Assessing Liver Tissue Fibrosis With an Automatic Computer Morphometry System;" Yung-Nien Sun and Ming-Huwi Horng; May/Jun. 1997.

* cited by examiner

DEVICE FOR THE QUALITATIVE EVALUATION OF HUMAN ORGANS

TECHNICAL FIELD OF THE INVENTION

The present invention relates to a device and method for qualitatively evaluating liver grafts. It concerns, in particular, the field of liver transplants between humans and the treatment of obesity.

STATE OF THE ART

In attempted liver transplants between humans, the donor's liver sometimes shows qualitative alterations that could compromise the recipient's life. In particular, a steatosis level above a certain limit value, for example 50%, is generally considered incompatible with transplantation. A steatosis level below this limit value but above a second limit value, for example 35%, imposes a preliminary lowering of the fat before a transplant.

However, obtaining biological data and decision-making, generally by the surgeon in charge of the implant, impose delays and costs, especially for travel, that are detrimental to the successful completion of the transplantation. In addition, visual estimation is not reliable, and performing biological analyses imposes delays that are detrimental to the quality of the liver.

A rapid, accurate evaluation of hepatic steatosis (HS) by transplant is of paramount importance for reducing the risks of liver dysfunction after a transplant. Histopathological analysis of the biopsied liver, which, though invasive, is the reference examination for evaluating HS, takes a lot of time and requires tools that are not always available. Because little time is available between the removal of the liver and the transplant, surgeons evaluate the HS by means of a clinical evaluation (medical history, blood analyses) and a visual analysis of the liver's texture. Although visual analysis is recognized as a challenge in clinical literature, very little effort has been directed towards developing computer-assisted solutions for evaluating HS.

With regard to the treatment of obesity, there are no means likely to give a diagnosis, in particular a steatosis level, immediately.

SUBJECT OF THE INVENTION

The present invention aims to make a method for qualitatively evaluating human livers that is portable and affordable, and to remedy all or part of these drawbacks. To this end, according to a first aspect the present invention envisages a device for qualitatively evaluating human livers, which comprises:
- a means for capturing an image of a liver, with the liver being in the donor's body, already removed, or placed in a hypothermic, normothermic and/or subnormothermic graft perfusion machine, when the image is captured;
- an image processing means configured to examine at least one portion of the liver's image from the captured image; and
- a means for estimating the health of the liver, based on the extracted image;

in which the estimation means is configured to apply the results of training about the characteristics of the image comprising color values measured in the image extracted to assign a quality evaluation to the liver represented by the captured image.

Thanks to these provisions, before removing or transplanting the liver, one automatically estimates whether this liver is sufficiently healthy so that transplanting this liver is beneficial for the recipient. Similarly, for treating obesity, one immediately has an objective estimate of the steatosis level of the patient's liver.

In some embodiments, the estimation means is configured to apply the results of training about the characteristics of the image comprising pixel numbers extracted from the image corresponding to predefined color values forming components representative of the extracted image, to assign a quality evaluation to the liver represented by the captured image.

Thanks to these provisions, the evaluation of the liver's quality is especially accurate.

In some embodiments, the evaluation means is configured to compute a value representative of steatosis of the liver, said value being a linear combination of pixel numbers of color values, referred to as components, i.e. at the level of a histogram of the image for the color component, numbers assigned multiplicator coefficients.

In some embodiments, the estimation means is configured to use, as principal components, a higher number of components for the values relating to the color red than for each of the colors blue or green.

In some embodiments, the coefficients for the green color are, on average, negative and have a greater absolute value than for the other colors.

In some embodiments, the coefficients for the green color have a mean below the mean of the coefficients for the other colors.

In some embodiments, the coefficients for the blue color have a mean above the mean of the coefficients for the other colors.

In some embodiments, most of the components correspond to color levels below the mean of the color levels in the histograms.

In some embodiments, the number of components is less than one fifth of the number of color levels.

In some embodiments, the device that is the subject of the invention comprises a means for estimating a confidence index representative of an average error for the estimation of the liver's health.

In some embodiments, the device that is the subject of the invention comprises a means for estimating the sharpness of the captured image, separate from the liver image capture means, and a means for communicating a sharpness index to the image capture means.

In some embodiments, the means for estimating the sharpness of the captured image is configured to utilize Sobel filtering.

In some embodiments, the image processing means comprises a means for selecting an image portion.

In some embodiments, the device also comprises a means for introducing into the donor's body at least one optical window of the means for capturing an image, as well as a source of light to illuminate the donor's liver, while preserving the sterility of the operation area.

In some embodiments, the image processing means comprises the application of a cropping mask to the captured image.

In some embodiments, the processing means comprises a means for generating the cropping mask, by processing colors and/or contours in the captured image.

In some embodiments, the processing image is configured to detect at least one reflection on the surface of the liver in the captured image, and to extract from the image at least one area presenting such a reflection.

In some embodiments, the means for estimating the health of the liver comprises a means for producing a histogram of colors, and a means for comparing at least one color of this histogram with a normalized color.

In some embodiments, each normalized color is borne by a color chart introduced into the field of the captured image.

In some embodiments, the means for estimating the health of the liver comprises a means for producing a sample of textures, and a means for comparing at least one texture with a reference texture.

In some embodiments, the means for capturing an image is a mobile telephone.

In some embodiments, the means for capturing an image comprises a flash light source, and is configured to capture an image with actuation of the light source.

In some embodiments, the device also comprises a sterile cover configured to contain an image capture means and comprising a rigid transparent capturing window to be positioned in front of the lens unit of the image capture means.

In some embodiments, the sterile cover comprises a polarizing filter to be positioned facing a light source, and a polarizing filter to be positioned facing the lens unit of the image capture means.

According to a second aspect, the present invention relates to a method for qualitatively evaluating human livers, which comprises:
  a step of computing normalized histograms of color channels from a portion of a photograph of a liver;
  a step of loading coefficients obtained at the end of a training phase;
  a step of extracting from the histograms values corresponding to variables retained at the end of the training phase;
  a step of computing a linear combination of the extracted values weighted with the loaded coefficients; and
  a step of displaying information representative of the result of the computation of the linear combination.

As the particular features, advantages and aims of this method are similar to those of the device that is the subject of the invention, they are not repeated here.

In some embodiments, during the display step the computed result is displayed in an interval centered on the result and having a width equal to twice the standard deviation from the training phase.

In some embodiments, the method that is the subject of the invention also comprises a step of normalizing values of the reduced centered histograms, with the mean and standard deviation values from the training phase.

BRIEF DESCRIPTION OF THE FIGURES

Other advantages, aims and characteristics of the present invention will become apparent from the description that will follow, made as an example that is in no way limiting, with reference to the drawings included in an appendix, in which.

DESCRIPTION OF EXAMPLES OF REALIZATION OF THE INVENTION

Figure 1:
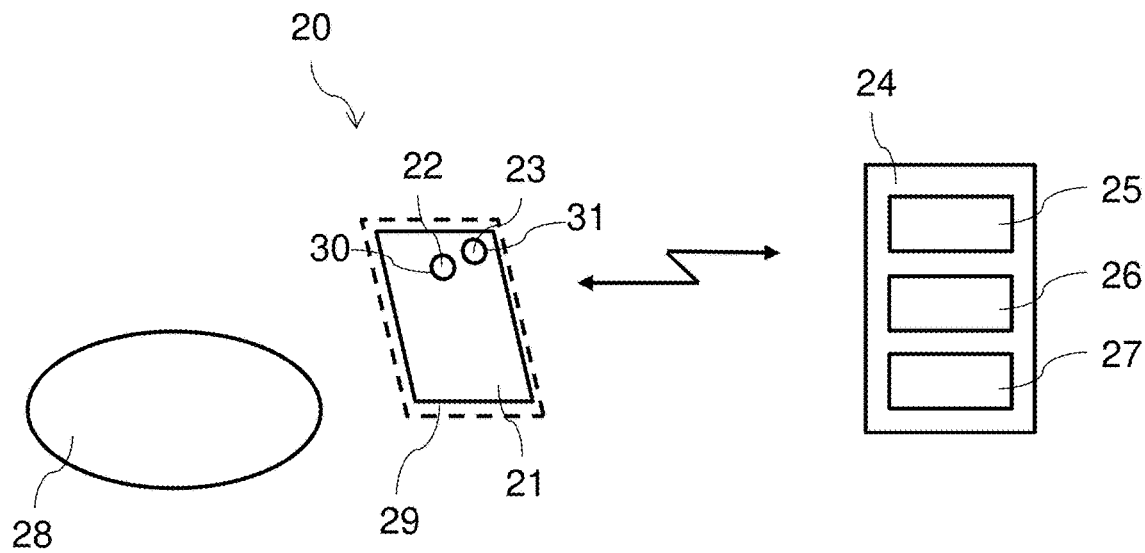
FIG. 1 represents, schematically, a first embodiment of an evaluation device that is the subject of the invention.

Hepatic steatosis (HS) is one of the most important characteristics of the donor that can affect the functioning of the graft and therefore the result of the liver transplantation (also referred to below as "LT"), mainly because of ischemia lesions and reperfusion during the transplant. Defined as the intracellular accumulation of triglycerides leading to the formation of lipid vesicles in the hepatocytes, HS is currently evaluated by histopathological examination of liver tissue samples obtained by biopsy. Through visual analysis by microscope of the amount of large-sized lipid droplets in the sample, an HS score is quantitatively assigned as a percentage (for example, 10% or 30%). Livers classified as having 5-30% fatty infiltration are linked to reduced survival of the patient and the graft, but they are still considered suitable for transplantation because of the limited availability of donors. Severe HS (≥60%) is strongly linked to a failure or primary non-functioning of the graft, and is not suitable for transplantation.

Although histopathological analysis of the biopsied liver tissue is currently the benchmark method for diagnosing and classifying HS in liver transplants, it is invasive, lengthy and costly. Because of the short time available between the liver removal and the transplantation, the surgeon normally estimates the HS by means of a clinical evaluation (medical history, blood analyses) and a qualitative visual evaluation of the transplant. In this context, the visual analysis of the liver's texture is recognized as fundamental in HS classification: livers that cannot be transplanted because of high HS usually have a non-uniform texture and are yellower than those which can be transplanted. However, it is acknowledged that accurately estimating HS remains difficult, even in experienced hands.

Against this background, it is necessary to develop a method that is robust, qualitative, practical, cost-effective and rapid to help the surgeon decide whether liver grafts must be accepted or rejected. In view of the challenges of the diagnosis, initial approaches to the automated or semi-automated evaluation of HS have been proposed and a complete review can be found in the literature. For example, analysis of the relationship between hepatic and splenic density has shown a sensitivity (Se) of 79% in recognizing the HS level, whereas FibroScan returned an area under the curve of 75%. Analysis of the bioelectrical impedance of the liver and Raman spectroscopy have also been used. A semi-automatic approach to classifying the HS using magnetic resonance spectroscopy (MRS) has been proposed, achieving a Spearman correlation coefficient of 0.90.

It should be noted that all the methods proposed require additional imaging instruments, which are not always available in organ removal centers. In addition, at most, the methods concluded that that there was a correlation between the physical characteristics of the liver (for example, rigidity and impedance of the liver) and the HS level, without providing a solution for evaluating the quality of the liver graft.

In some embodiments, the present invention envisages a device 20 for qualitatively evaluating human livers, which comprises, as shown in FIG. 1:
- a means 21 for capturing an image of a human liver 28, with the liver being in the donor's body, already removed, or placed in a hypothermic, normothermic and/or subnormothermic graft perfusion machine, when the image is captured;
- an image processing means 25 configured to extract at least one portion of the liver's image from the captured image; and
- a means 26 for estimating the health of the liver, based on the extracted image.

Figure 4:
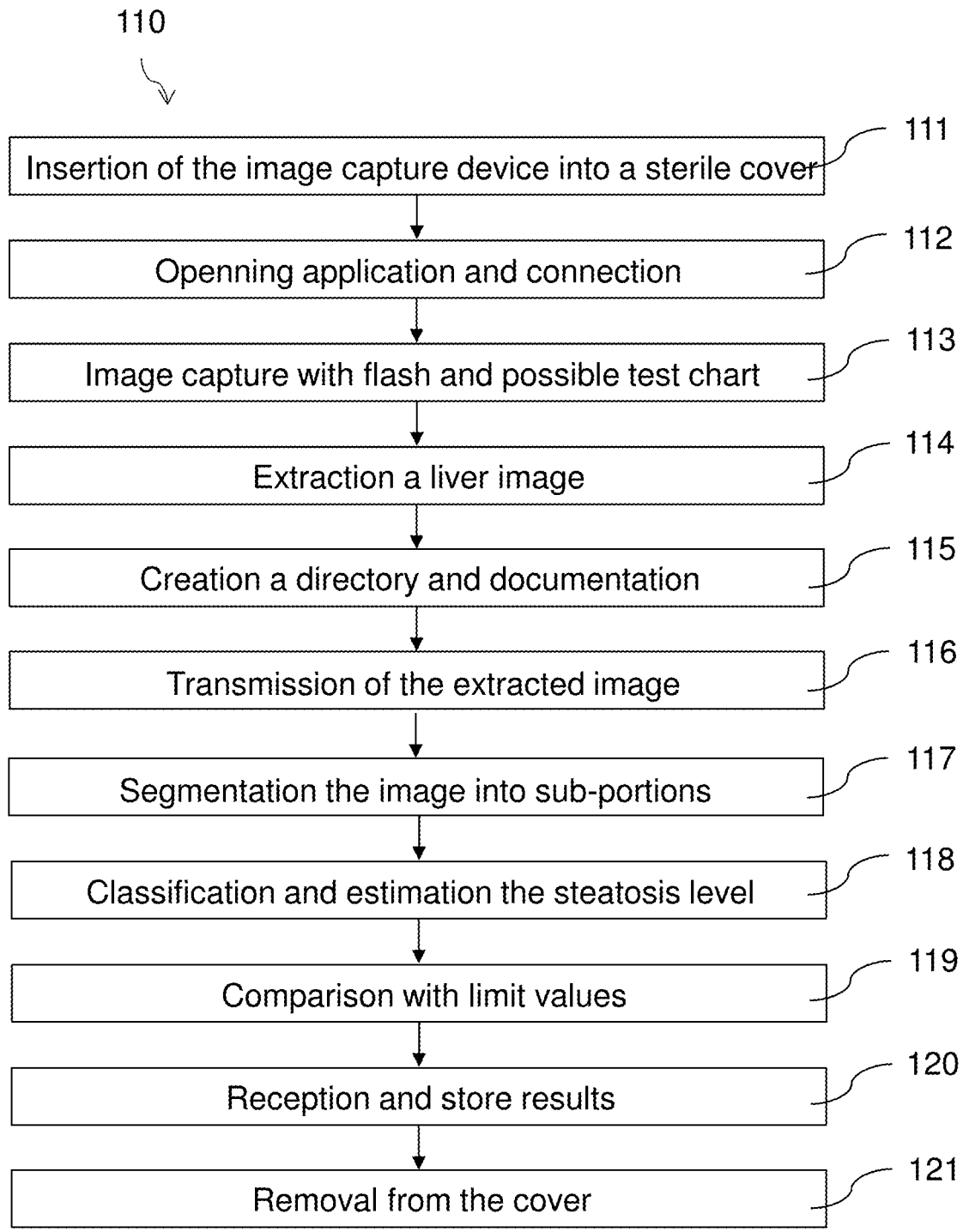
FIG. 4 represents, in the form of a logic diagram, steps in extracting an image of a liver in a captured image.

Depending on the embodiments, the liver being evaluated for quality is:
- in the body of the donor, whose abdominal organs are visible after incision of the skin, as illustrated in FIG. 4;
- in the body of the donor, the liver being observed by means of an endoscope inserted into a trocar, the donor's abdomen being inflated to perform a coelioscopy; or
- already removed from the donor's body and possibly in a graft perfusion machine.

In the embodiment shown in FIG. 1, the image capture means 21 is a digital camera or, preferably, a smartphone. This image capture means 21, fitted with an optical window 22 on the front lens of its lens unit and a flash light source 23, is preferably inserted into a sterile protective cover 29.

The materials used for the cover can be polyethylene, polyurethane or silicone with tactile qualities preserved. The surface of the cover can be covered with antibacterial and fungicidal agents. The cover is closed by adhesive (system for folding one side of the cover and gluing). The cover is compatible with all smartphones in a predefined range of dimensions. Note that, with the materials selected, there are no specific features for the optical window positioned in front of the image capture device. The user presses the cover against the optical window before taking the image.

In some embodiments, the sterile cover 29 comprises a polarizing filter 31 which, during the insertion of the smartphone, is positioned facing a light source, and a polarizing filter 30 which is positioned facing the lens unit. Thus, in some embodiments, the evaluation device that is the subject of the invention also comprises a means for introducing into the donor's body at least one optical window of the means for capturing an image, and for introducing a source of light to illuminate the donor's liver, while preserving the sterility of the surgery area.

In the case where the endoscope is used, the photo is acquired solely by the endoscope, not by a smartphone. However:
1) The photo taken by the endoscope can be retrieved by a wired or non-wired (for example, using one of the Bluetooth or Wi-Fi protocols, registered trademarks) connection between the console retrieving images from the endoscope and a smartphone for sending data to a program implementing the algorithms described below, and immediately having the result concerning the steatosis level.
2) The algorithms can be incorporated directly into the image retrieval console, and can provide a real-time result for the steatosis level on the coelioscopy screen (no smartphone is used in this case).

All photos taken with the endoscope are normalized (white balance at the start of the intervention, light uniform, and thus better in terms of quality).

In other embodiments, the image capture means comprises glasses incorporating an electronic sensor.

The image processing means 25 is located either in the image capture means (for example in the image retrieval means or in the smartphone, case not shown), or on a remote server 24 equipped with an image store 27 and a central processing unit utilizing a mask, determined automatically or fixed. A logic diagram of automatic masking is described with regard to FIG. 5.

The liver health estimation means 26 is located either in the image capture means, or in the remote server 24 equipped with an image store 27 and a central processing unit utilizing an algorithm detailed below, especially with reference to FIGS. 2 and 3.

Thanks to the utilization of the device that is the subject of the invention, before removing or transplanting the liver, there is an automatic estimation of whether this liver is sufficiently healthy so that transplanting this liver is beneficial for the recipient. There is therefore no need for the surgeon in charge of the transplantation to travel or carry out a purely visual evaluation to accept the liver or to have it treated with a view to its transplantation. Similarly, for treating obesity, the device provides the surgeon with an immediate estimate of the steatosis level of the patient's liver.

Figure 8:
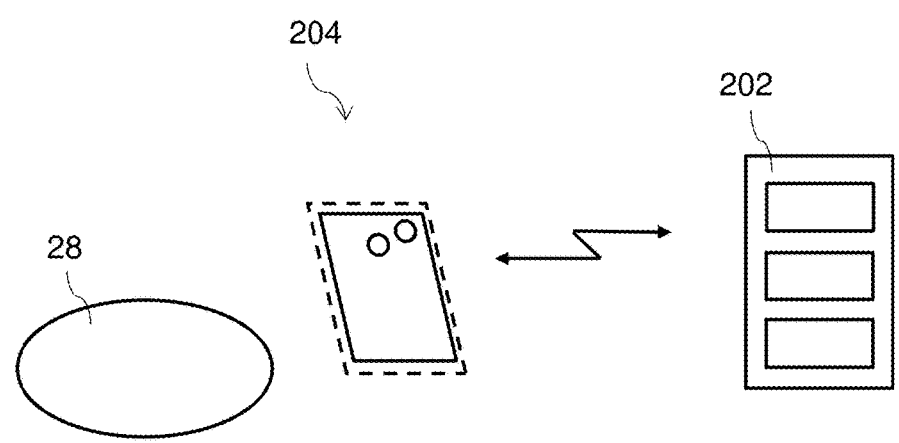
FIG. 8 represents systems utilized in a particular embodiment of the method and device that are the subjects of the invention.

FIG. 8 shows a system 200 to help take good-quality images, i.e. sufficiently sharp and covering a liver area with a dimension greater than 6 centimeters, and preferably at least two-thirds of the liver, i.e. approximately 19 cm wide and 10 cm high, and, even more preferably, the entire visible portion of the liver. This system 200 comprises a server 202 in communication with an image capture device 204, typically a mobile telephone. Preferably, the server 202 controls the focusing of the lens unit of the image capture device 204 so as to have a sharp image at approximately 10 cm. In some embodiments, the autofocus of the image capture device is left free to perform the focusing.

Figure 9:
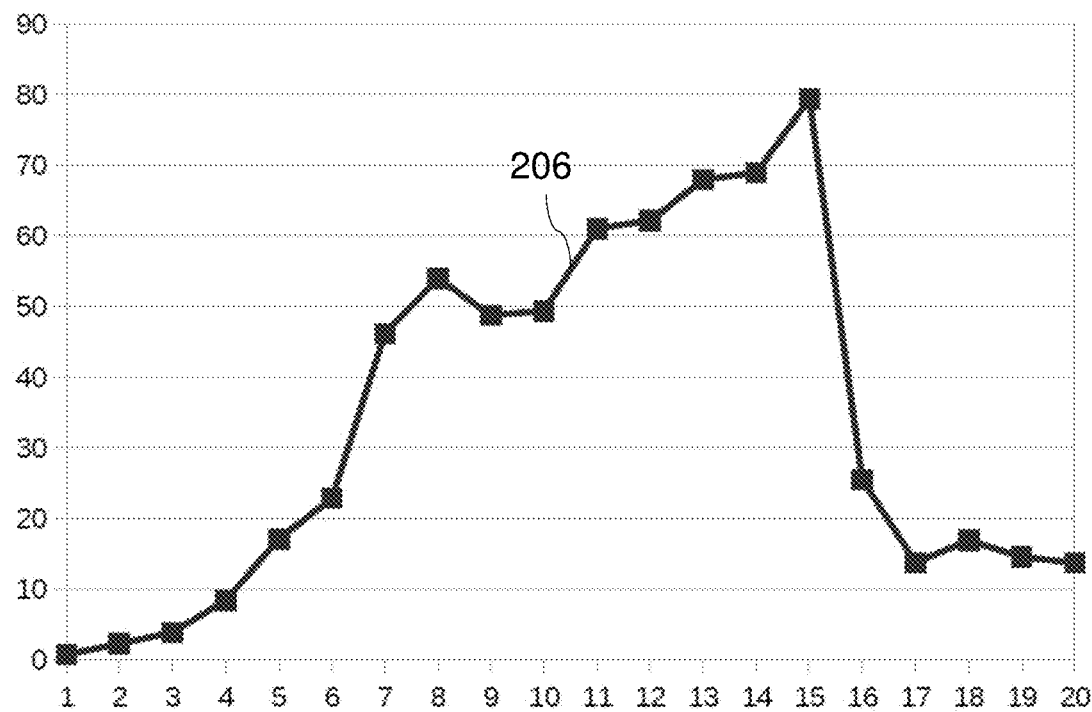
FIG. 9 represents a measurement curve for sharpness as a function of the image capture distance.

The server 202 receives a series of images captured by the image capture device 204 and determines whether the sharpness of each image is sufficient to allow a qualitative evaluation of human livers. For this purpose, the server 202 determines the result of the Sobel filtering applied to at least one portion of the image corresponding to the liver, or to the entire image. The result of the Sobel filtering is compared to a predefined limit value, for example 40. FIG. 9 shows the curve of the results 206 from the use of the Sobel filter as a function of the distance, in centimeters, between the lens unit of the image capture device 204 and the liver 28 for which an image is captured. It can be seen that, at the shortest distances, the image is blurred because the focusing distance of the image capture device does not enable a sharp image capture. In addition, at the shortest distances, the captured image does not cover a large enough portion of the liver and therefore does not show its contour. In contrast, at the longest distances, the blurring is because the image's details of the liver's texture are no longer visible. Between these extremes—for example, in the case of the image capture device and the focal length used, between seven and fifteen centimeters—the image has the extent and sharpness necessary for image processing. If a Sobel filtering limit value equal to 60 is chosen, the images captured between eleven and fifteen centimeters meet the sharpness criterion.

Based on the result of comparing the Sobel filtering value with the predefined limit value, the server 202 sends a message representative of the sharpness and therefore of the capacity to capture an image to a dedicated application installed on the image capture device 204. In a variant, the image that meets this sharpness criterion is returned by the server 202 to the image capture device 204 for displaying to its user on a screen.

Note that the Prewitt and Roberts filtering algorithms also give good discrimination for images that are sufficiently sharp. However, the Roberts algorithm needs more elementary operations.

Figure 10:
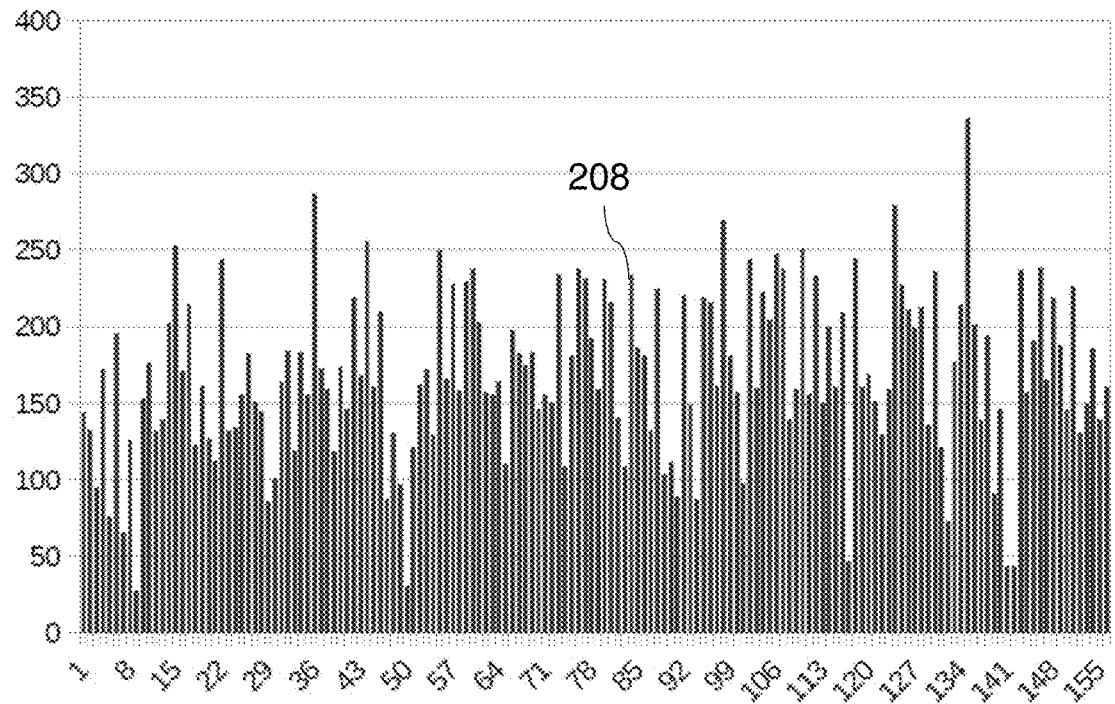
FIG. 10 represents sharpness measurement results of photos of human livers.

FIG. 10 shows the results 208 of the Sobel algorithm on a set 156 of photos of human livers, after a single portion of the image is used. In effect, the inventors have discovered that, in the images captured, there are often smooth tissues that reduce the Sobel filtering value for the entire image.

In some preferred embodiments, only a portion of the captured image is taken into account, for example the quarter of the image having the highest Sobel filter value. In this embodiment, the image is divided into four equal portions, on either side of a central vertical line and either side of a central horizontal line, and the Sobel filtering value is determined for each of these portions. Then only the highest value of the four values obtained is retained.

Note that, with the experimental means utilized, compliance with the sharpness criterion by the server is determined, on average, in 0.07 seconds per complete image, which allows an almost instantaneous response to be provided to the image capture device 204.

Figure 11:
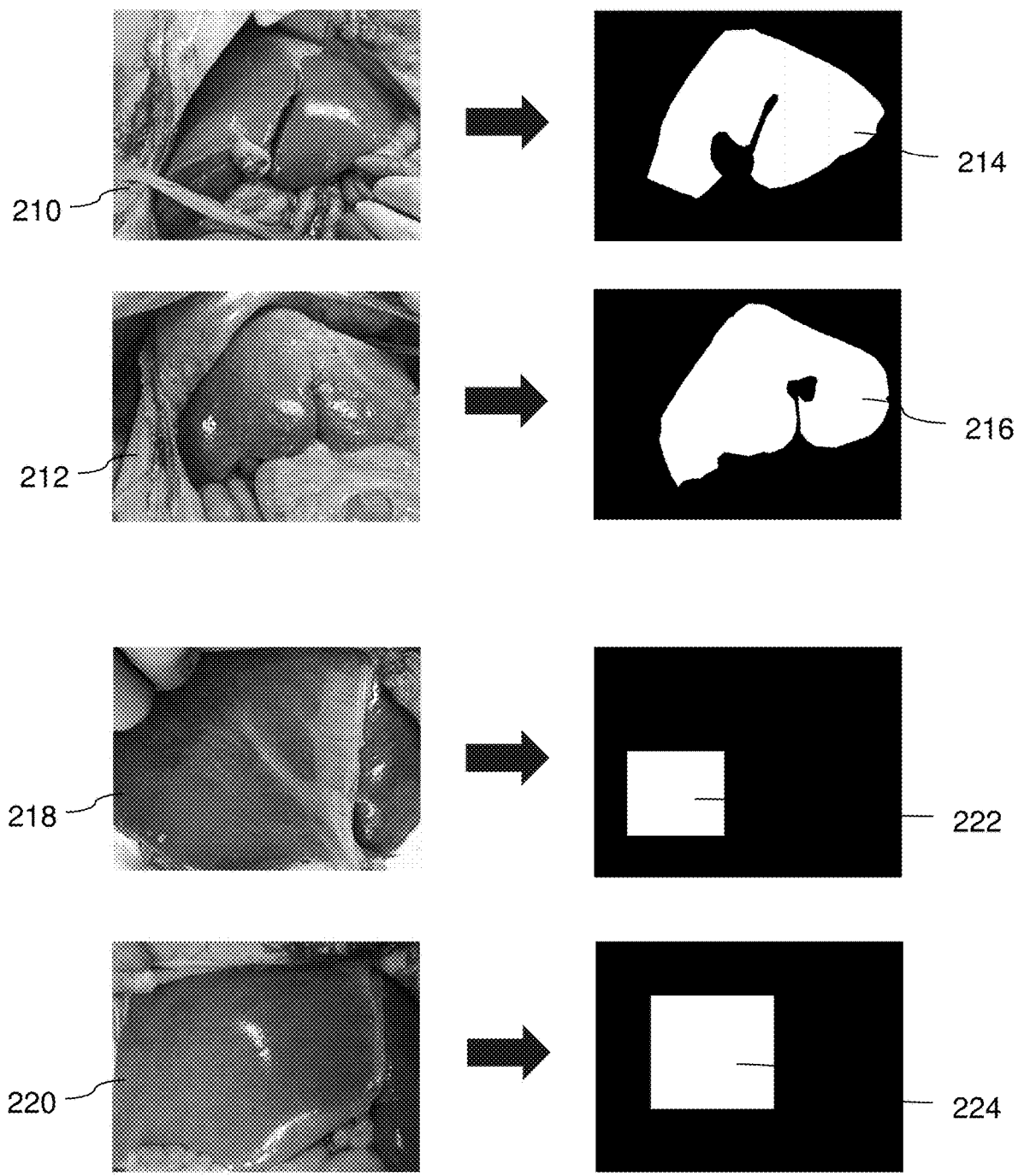
FIG. 11 represents masks generated automatically or by an operator, with regard to photographs of livers.

Once the image of the liver has been captured with the level of sharpness meeting the criterion described above, a first mask is applied to the image so that the portions of the image not representing the liver are not considered. To this end, in some embodiments, automatic detection of the portion of the image that represents the liver is performed by automatic cropping. The liver images 210 and 212, in FIG. 11, therefore correspond to the masks 214 and 216. In other embodiments, the user, for example the surgeon, positions a first rectangular (or any other predefined shape) mask on the captured image. This first mask represents an area of interest that the surgeon considers to be relevant in determining the quality of the liver. The liver images 218 and 220, in FIG. 11, therefore correspond, for example, to the first masks 222 and 224.

Preferably, the user is prevented from selecting an area of interest that is too small and there is a requirement, for example, that the width or height of the area selected be at least greater than six centimeters over the liver. Thanks to this mask, at least one dimension of which is greater than six centimeters over the liver, in which only the portion of the liver image shown in white is kept for subsequent processing, heterogeneity of the liver is removed.

This sizing characteristic is very different from that of a biopsy, which covers at most two centimeters. The biopsy therefore adds a subjective step of choosing the sampling area. In addition, in biopsies, the temperature (cold) and the stabilizers required for conservation modify the results and taint them with errors or, at least, variability.

White spots in the image, which relate to reflections, and shadows are then removed. Preferably, to perform this removal, a filter adaptive as a function of the mean luminance value of the image, or of a portion of the image, is utilized to compensate for the differences in lighting.

In this way, only the values of the pixels whose luminance is above a first predefined limit value, to remove the shaded areas, and below a second predefined limit value, for example 170 on each channel, to remove the white areas, are kept.

In some variants, for eliminating shadows, the luminance value of the point is replaced by the maximum luminance value of the points of a neighborhood surrounding the point in question, and the points whose values, on each channel, are below 50 or 60 on each channel, for example, are removed.

In these examples, the pixels whose maximum value on the three channels R, G and B is less than 50 or 60 or whose minimum value on the three channels is greater than 170 are therefore removed. Therefore, a pixel with an RGB value of (207, 22, 75) would be accepted and would contribute to the 207 value of the red histogram, the 22 value of the green histogram, and the 75 value of the blue histogram.

The images that result from this processing are in the form of matrices, certain points of which, eliminated in this way, have a value representative of their elimination, for example "0". Each other point, not eliminated, is associated to three values, for example in eight bits, representative of the red, green and blue channels.

The server then automatically determines an additional mask, of a predefined shape, for example circular or elliptical, at least one dimension of which corresponds to a distance on the liver of at least six centimeters.

Possibly, a dilatation is performed, for example up to a distance of 15 pixels wide and 4 pixels high. The mask and the dilatation function are applied on each pixel of the image. The aim is to take the neighboring pixels into account and therefore to erase the defects and irregularities of the image by means of a blurring phenomenon. On the image, a dilation function is therefore applied in this additional mask to erase the defects and their neighborhood.

Lastly, on the resulting image, the histograms of values for each of the red, green and blue channels are extracted.

In order, in some embodiments, to normalize intensity of the histograms of images, using luminance normalization, the histogram of each RGB channel is retrieved and the first value is removed. The three histograms for a single image are placed in a single vector. The total sum of the values in the vector is computed. Each value of the histogram is divided by the total sum.

The normalization in number of pixels is performed by dividing each pixel number for a color level by the number of pixels taking part in the histogram.

Note that luminance normalization is, in some embodiments, performed before the thresholding of extractions of reflections and shadows, to make them more stable. In some embodiments, a first luminance normalization is performed before thresholding and a second luminance normalization is performed on the image after thresholding.

The three histograms are processed independently to constitute a vector of three times 255 values, i.e. 765 values. A smoothing is applied to this triple histogram, or vector, by replacing, for each color level, the number of pixels having this color level by the mean or median number of pixels for this level and the two levels just above or just below, respectively.

In some embodiments, in place of or in addition to the use of an additional mask, an automatic detection of points or areas of interest is utilized, which consists of highlighting areas of this image judged "Interesting" for the analysis, i.e. having notable local properties. Such areas can appear, depending on the method used, in the form of points, continuous curves, or connected regions, which constitute the result of the detection.

After the detection, a description algorithm, which will focus on each area of interest detected, is applied to compute their features (digital, in general).

The most common method for its detection is probably the Harris detector.

Like the Harris detector, most of the other techniques of detecting points of interest are based on a local analysis of the image at order 2. What differentiates them from each other is the derivation operator used. Methods based on DoG (Difference of Gaussians), LoG (Laplacian of Gaussian) or DoH (Difference of Hessians) analysis can be cited.

The regions of interest are more general areas of interest than the points, useful when the structures sought in an image are not prominent points, for example when the image has undergone significant smoothing or when the contours are thick and feathered.

Frequently, these techniques begin by identifying points of interest that will prove to be sorts of barycenters of the regions sought (blobs), such as multi-scale methods based on the study of the detectors of points of interest mentioned above (Harris, DoG, etc.), at different scales of the image. This makes it possible to obtain circular or elliptical regions, depending on the level of refinement desired. These methods are often incorporated into more general algorithms, such as SIFT or SURF, which include a region of interest descriptor as well as a detector.

Among the more general region of interest detectors there is also MSER (Maximally Stable Extremal Regions).

Steps of training and then qualitatively evaluating human livers, in particular embodiments of the invention are described below.

The components ("features") selected for the training are, as explained below, the values from RGB histograms. Based on a set (for example thirty) of images of livers whose quality has been classified, in terms of steatosis, by experts and/or by known techniques, such as biopsies, sparse learning is performed.

The variable y is the result of the steatosis predicted by the algorithm.

$$y = b0 + \Sigma_{k=1}^{xV} bk * Xk$$

Figure 16:
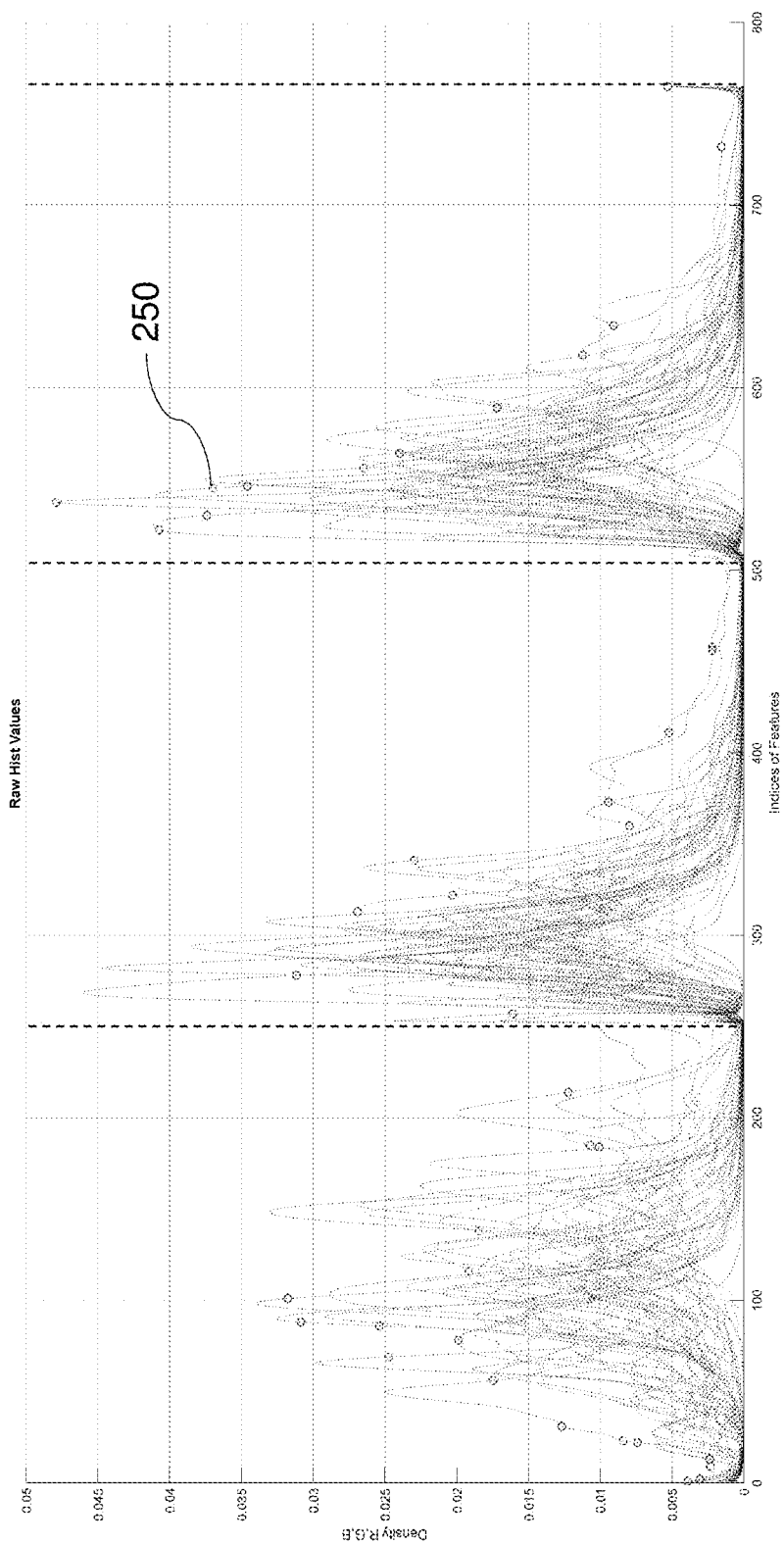
FIG. 16 represents a set of histograms for liver photographs and the position of the variables selected.

Where:
b0 is a fixed value (b0=28.4 for example);

xV is the set of components processed (in this case forty, but the inventors have noted that, with an increasing number of examples in the learning database, this number stabilizes around 90). Preferably, the number of principal components chosen is less than one-fifth of the number of components;

bk are the multiplicator coefficients associated to the components processed (see FIG. 14); and Xk is the number of pixels of the image portion processed having a color value corresponding to a principal component, i.e. to a level of the histogram of the image being processed for the color component in question (see FIG. 16).

This classifies y into one of three classes corresponding to ranges of steatosis values (0, 30), (30, 50), (50, 100), as described above.

These ranges are used to produce the final diagnosis by the surgeon. They make it possible to define if a liver is non-steatosic (healthy), y being in the range of values (0-30); average, y being in the range of values (30-50); or defective, corresponding to a one in two risk of the graft being rejected after transplantation, y being in the range of values (50-100).

b0 represents the roughest prediction in the absence of all information. It is simply the mean of the known steatosis values.

The bk factors are the results of the training algorithm on the images used for this training. Of course, another training algorithm could determine other principal components and other factors to be applied to them.

The person skilled in the art could adapt the invention, using a database of liver photos, image processing, followed by the training phase, to find coefficient values.

The values of y computed by the formula approximate observed steatosis values in the range of values (0, 100). Values of y less than 0 are brought back to 0, and values greater than 100 are brought back to 100. Next, the liver is classified into one of the 3 classes depending on whether the value of y is in the range (0, 30), (30, 50), (50, 100).

The algorithm was trained on a database of 33 photos with biopsies (variables). The objective of this test was to see the result of 54 photos tested without the biopsy, and then to compare the result of the biopsy (reference) with the result of the algorithm (3 classes).

In the first training step, y is predicted with the group of variables (three eight-bit histogram values, in three colors) by minimizing the number of selected variables. In the second step, y is predicted with all the selected variables.

After comparing the result between the reference biopsy and the result of the algorithm, a prediction error value is obtained.

In this case, the algorithm was trained using 40 variables or principal components.

Figure 12:
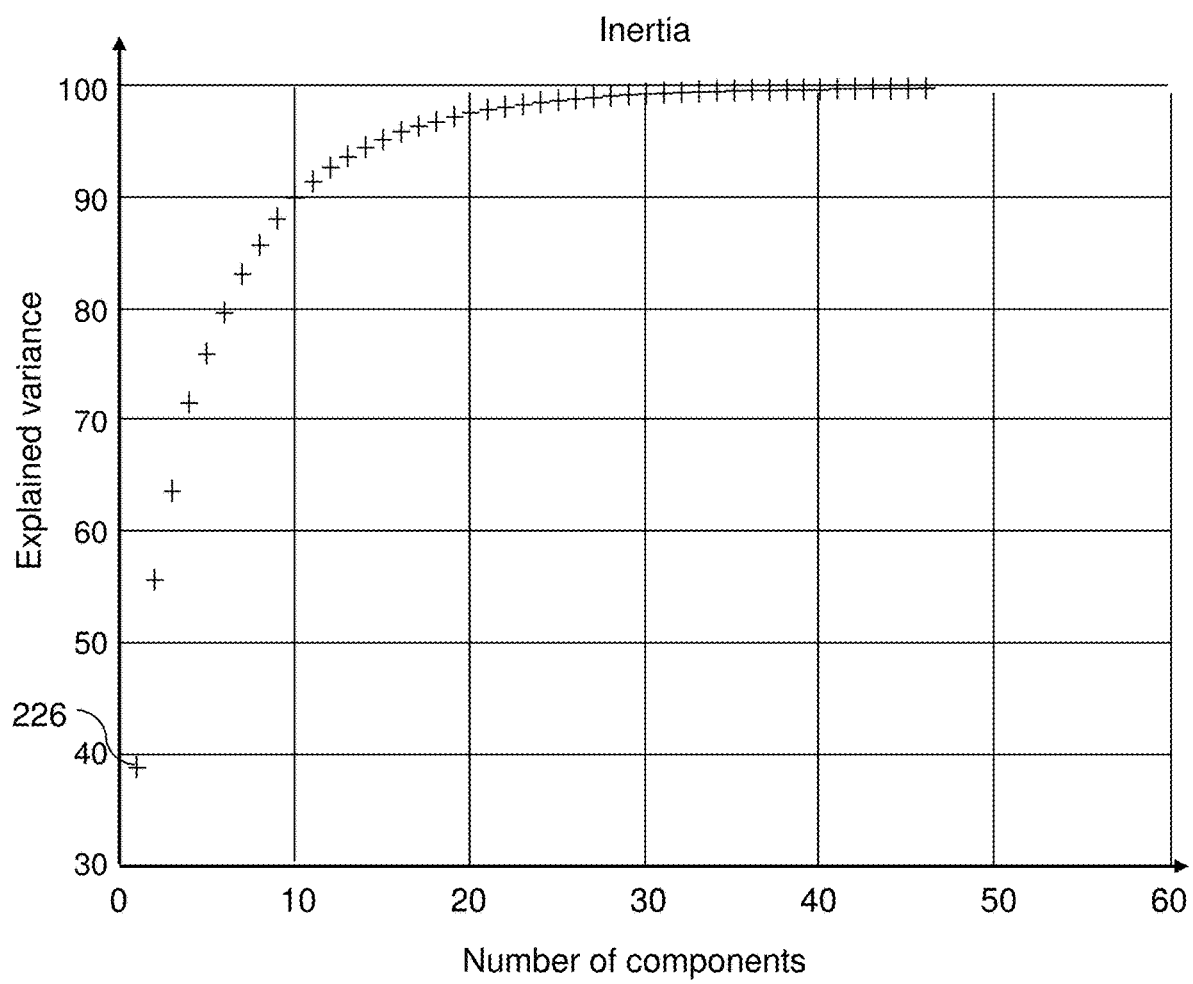
FIG. 12 represents a variance curve as a function of the number of components studied.

In this study, between 30 and 40 variables were used to have a result of over 95% positive predictions according to the three classes. To reduce this number of components, a principal component analysis is performed. As shown in FIG. 12, 40 components (color levels) are sufficient to represent 99% of the variance 226.

FIG. 12 indicates the proportion of the explained variance as a function of the number of principal components. With 30 principal components, 98% of the explained variance is obtained. It is an indicator of the number of features necessary to predict steatosis. It is important to note that we make the prediction based on features extracted from the image rather than based on principal components. However, the number of features selected, 40, is of the same order as the number of principal components, 30.

With regard to principal component analysis and "Sparse Learning", the reader can refer to the following works:

"Principal component analysis", Gilbert Saporta. *Probabilités, Analyse des données et statisque* (Probabilities, Data analysis and statistics). BOOK, Technip (Editions), 2011.

"The Elements of Statistical Learning: Data Mining, Inference, and Prediction", Trevor Hastie, Robert Tibshirani, Jerome Friedman—Springer, 2009.

"Sparse Learning", M. Jiu, N. Pustelnik, S. Janagi, M. Chebre, P. Ricoux, "Sparse hierarchical interaction learning with epigraphical projection", accepted to the Journal of Signal Processing Systems, 2019.

Figure 13:
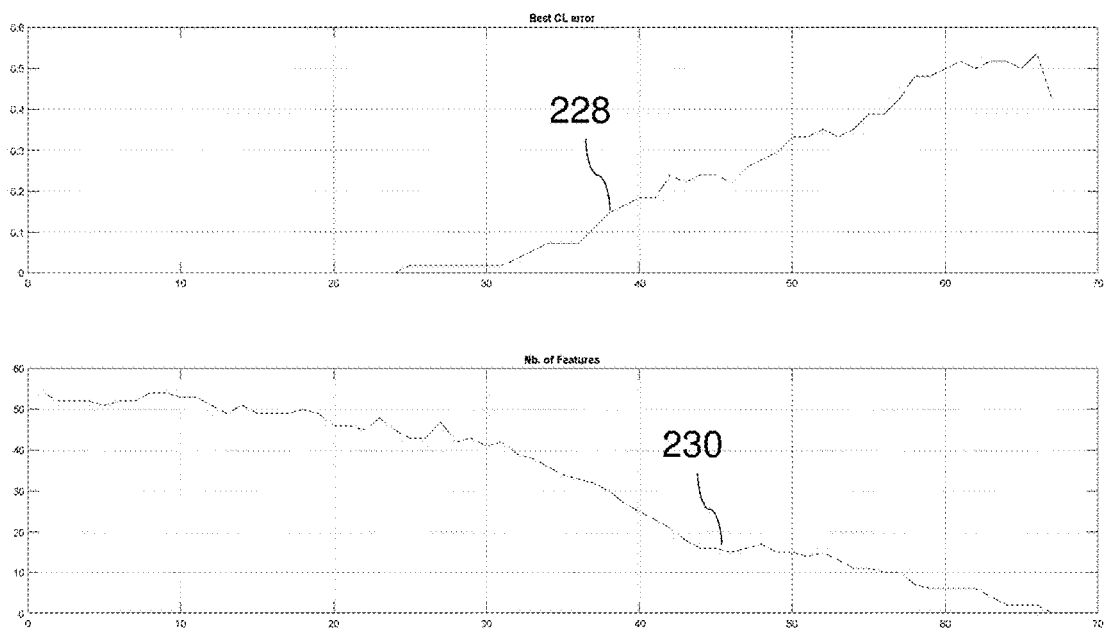
FIG. 13 represents a classification error as a function of the number of variables.

As illustrated in FIG. 13, the sparse learning procedure reduces the number of variables 230 (lower table) and tracks the classification error 228 (upper table). The intersection of the two trends is between 30 and 40 variables. The optimum chosen is 40 variables. As the number of features is reduced (lower axis), the prediction error increases. A compromise is found for 40 variables.

Figure 14:
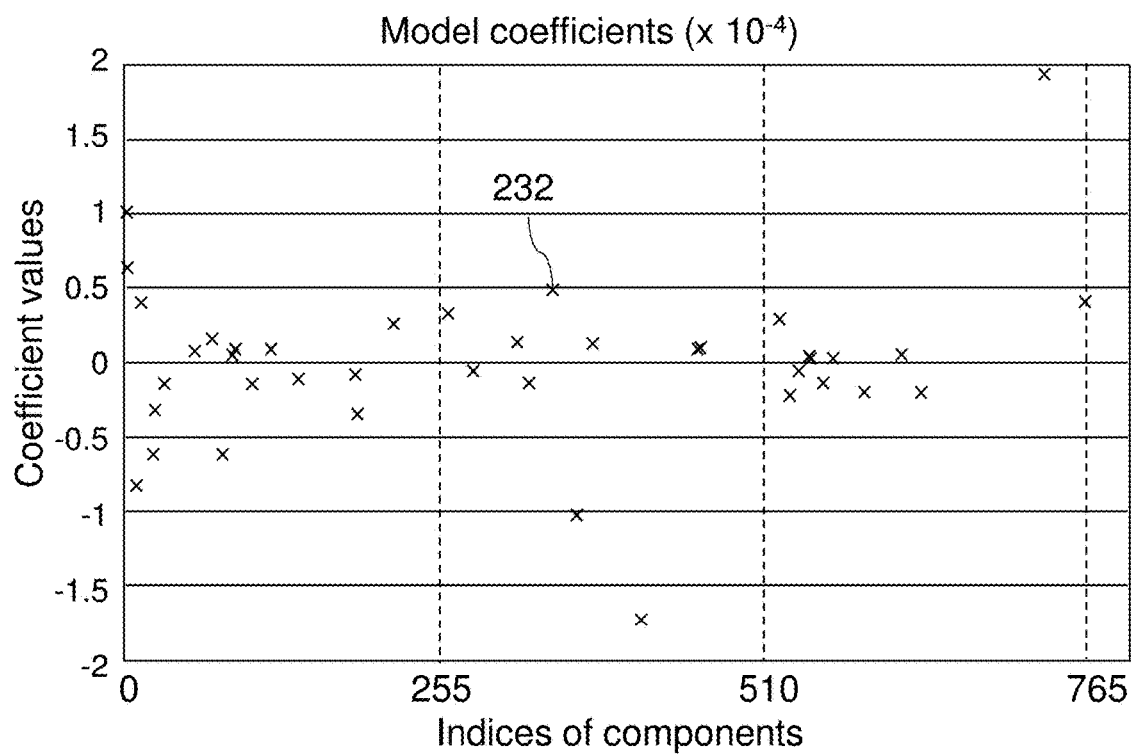
FIG. 14 represents values of coefficients determining an indicator of liver quality for forty variables selected by training.

FIG. 14 shows the non-zero bk coefficients 232 of the 40 variables chosen. The vertical dotted lines show the separations between the histograms corresponding successively to the colors red, green and blue, from left to right.

It can be seen that the bk coefficients have the following values, rounded to the first decimal place, after a multiplicator coefficient of 10,000 ($10^4$) was applied:

for the components in the histogram for the color red: 1.0; 0.6; −0.8; 0.4; −0.6; −0.3; −0.1; 0.1; 0.2; −0.6; 0.1; 0.1; −0.2; 0.1; −0.1; −0.1; −0.4; 0.3;

for the components in the histogram for the color green: 0.4; −0.1; 0.2; −0.2; 0.5; −1.0; 0.2; −1.7; 0.2; 0.2;

for the components in the histogram for the color blue: 0.3; −0.2; −0.1; 0.1; 0.1; −0.2; 0.1; −0.3; 0.1; −0.3; 1.9; 0.4.

It can be seen that the mean of the coefficients for the color red is between 0.0 and 0.05, for the color green below −0.1, and for the color blue above 0.1. It can also be seen that the mean absolute values of the coefficients for the color red is between 0.3 and 0.35, for the color green between 0.45 and 0.5, and for the color blue between 0.32 and 0.37. Therefore:

there are more variables, and thus bk coefficients, for the color red than for the other colors;

the bk coefficients for the green color are, on average, negative and have a higher absolute value than the other colors;

the bk coefficients for the green color have a mean below the mean of the coefficients for the other colors;

the bk coefficients for the blue color have a mean above the mean of the coefficients for the other colors;

the coefficients concern more often, and with a higher absolute value, the low (dark) color levels.

The device and method of these embodiments of the invention evaluate the quality of the liver by computing a value representative of steatosis of the liver, said value y being a linear combination of pixel numbers of color values, referred to as components, i.e. on a histogram of the image for the color component, numbers assigned multiplicator coefficients.

Preferably, the estimation means is configured to use, as principal components, a higher number of components for the values relating to the color red than for each of the colors blue or green.

In some embodiments, the coefficients for the green color are, on average, negative and have a greater absolute value than for the other colors.

In some embodiments, the coefficients for the green color have a mean below the mean of the coefficients for the other colors.

In some embodiments, the coefficients for the blue color have a mean above the mean of the coefficients for the other colors.

In some embodiments, most of the components correspond to color levels below the mean of the color levels in the histograms.

In some embodiments, the number of components is less than one-fifth of the number of color levels.

Figure 18:
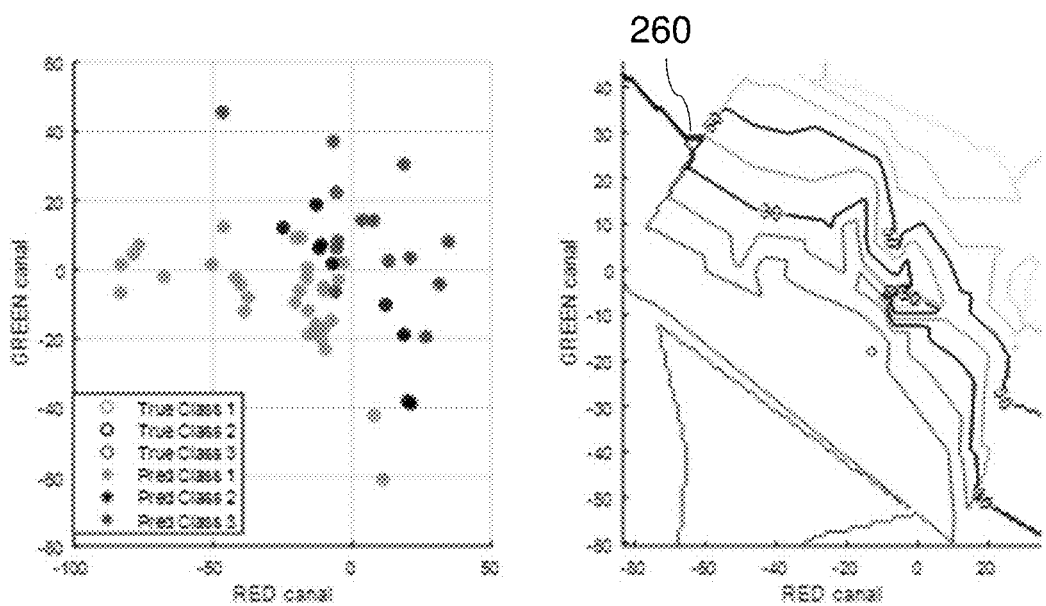
FIG. 18 represents trends observable according to representations.

Trends can be seen in FIG. 18. If the contribution R=sum (bk*xk) on the red channel, the contribution G=sum (bk*xk) on the green channel, and B=sum (bk*xk) on the blue channel are computed then, when the observations are plotted on the axes (R, G), (R, B), (G, B), a steatosis gradient 260 can be seen. The negative or positive values are the result of reduced centered normalizations of the histograms ("zscore" function in Matlab).

Figure 15:
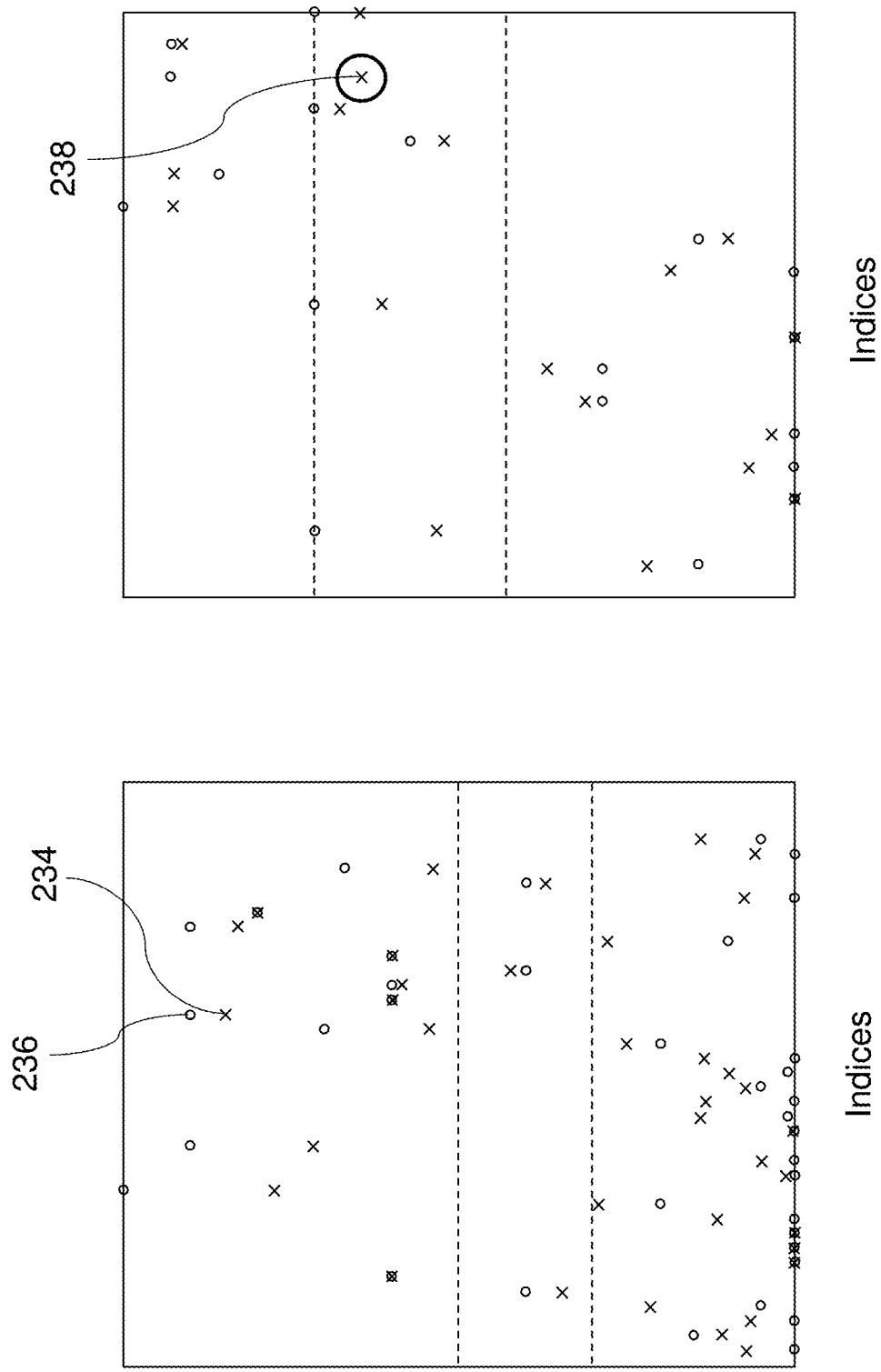
FIG. 15 is a table comparing steatosis values in three classes between the prediction produced by the method and the devices that are the subjects of the invention and the result observed on biopsy, on the left for the training images and on the right for the prediction images.

FIG. 15 shows the table comparing steatosis values in the three classes between the prediction 234 and the result 236 observed on biopsy, on the left for the training images and on the right for the prediction test images. The circled point 238 in the table on the right makes it possible to see the prediction error. This point should have been in the "above 50" class, but it is in the "between 30 and 50" class. Of course, with more test images, especially representing livers with a high steatosis level, this error could be avoided.

FIG. 16 shows all the histograms processed, together with the color levels that correspond to the 40 principal components. FIG. 16 shows all the livers on the histograms normalized, from left to right for the colors red, green and blue. The features used are shown by the circles 250.

A comparison of the RGB channels can be performed to understand the prediction results trend, by plotting contour lines.

Figure 17:
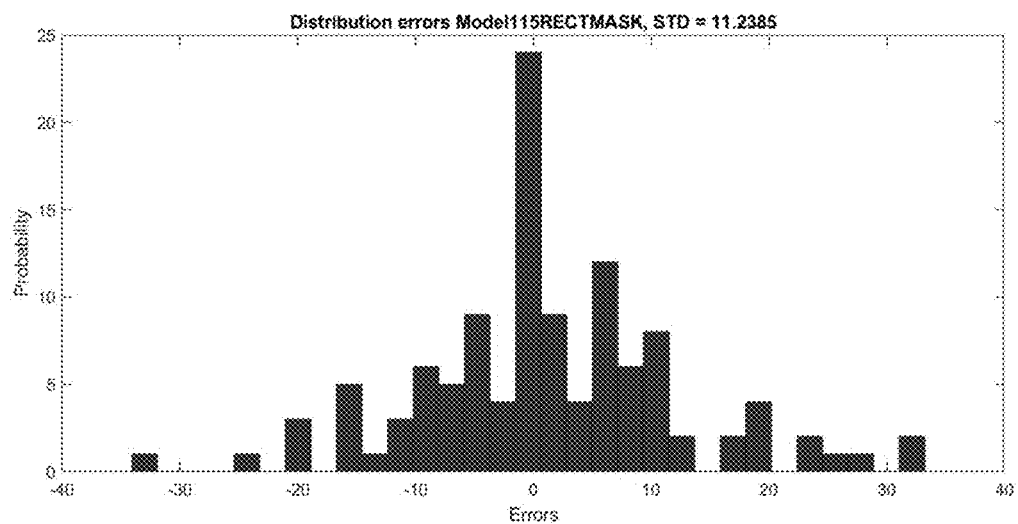
FIG. 17 represents a distribution of prediction errors.

With regard to processing errors, FIG. 17 shows the distribution of prediction errors. It can be seen that most of the images give a prediction error around 12% of steatosis. This gives an alternative steatosis value prediction+/−an error standard deviation. Or, more simply, a prediction in (Smin, Smax) interval form.

Note that the standard deviation in the comparison between an expert surgeon's evaluation by means of visual analysis and the result of the biopsy by an anatomical pathologist is 20%.

Figure 19:
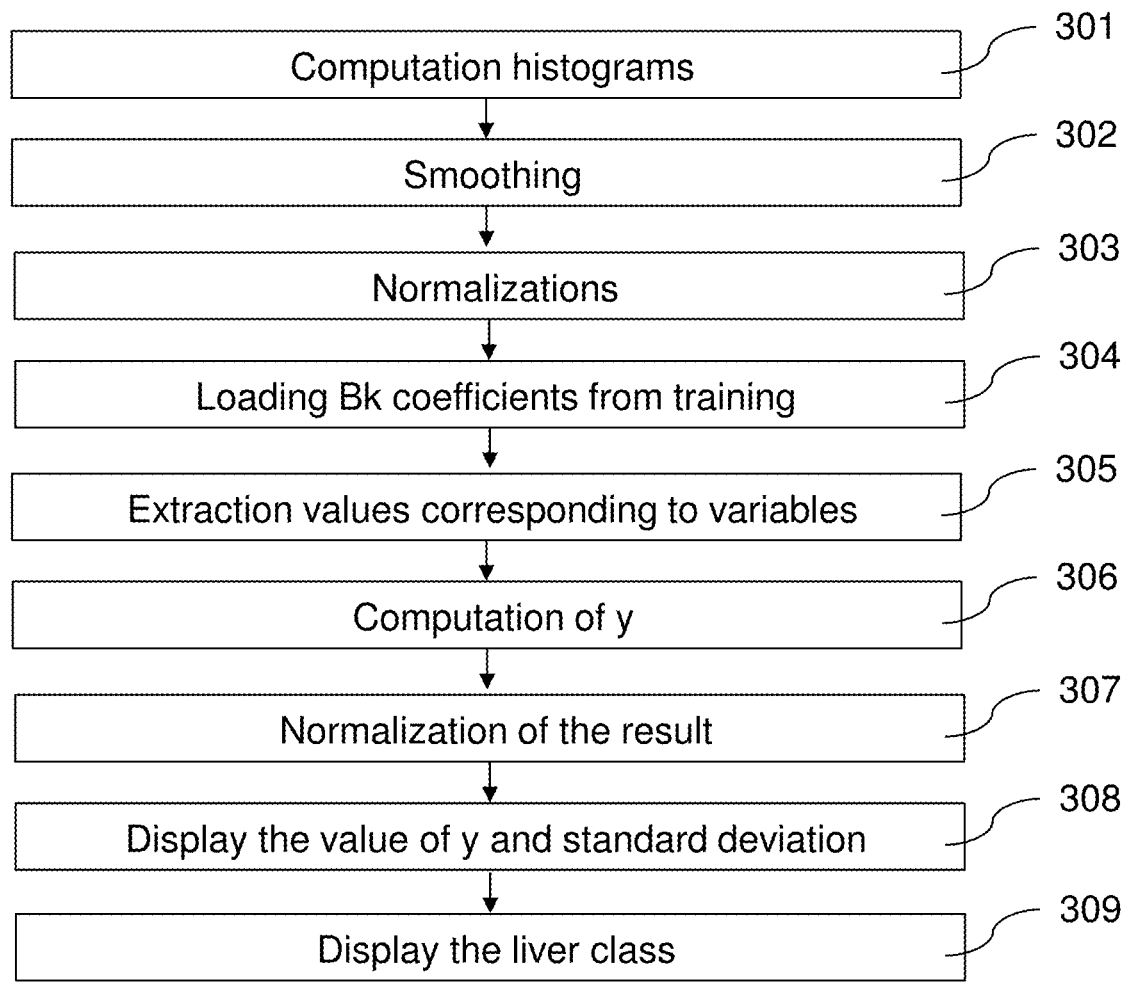
FIG. 19 represents, in the form of a logic diagram, steps in a particular embodiment of the method that is the subject of the invention.

In the method illustrated in FIG. 19, the following steps are shown:

step 301: compute the normalized histograms of the R, G, B channels from the image. The result is a vector x of 255*3=765 values;

step 302: smooth the values of the vector x by a sliding mean with window width 5 (this is a variant of the window 3 described above);

step 303: normalize the values of x by means of a reduced centered normalization with the mean and standard deviation values selected in the training phase from the training database;

step 304: load the b0, bk coefficients recorded at the end of the training phase;

step 305: extract the values of x(k), k=1, . . . , m, corresponding to the variables selected by the training phase;

step 306: compute y=b0+b1'x (1)+ . . . +bm*x(m);

step 307: if y<0 then y=0; if y>100 then y=100;
step 308: display the response [y−s, y+s], where s is the standard deviation of the error computed from the training database (here 12%);
And/or
step 309: display the response: if y is in [0, 30]—liver good (class 1); y is in [30, 50]—liver to be discussed (class 2); y is in [50, 100]—liver poor (class 3).

Figure 2:
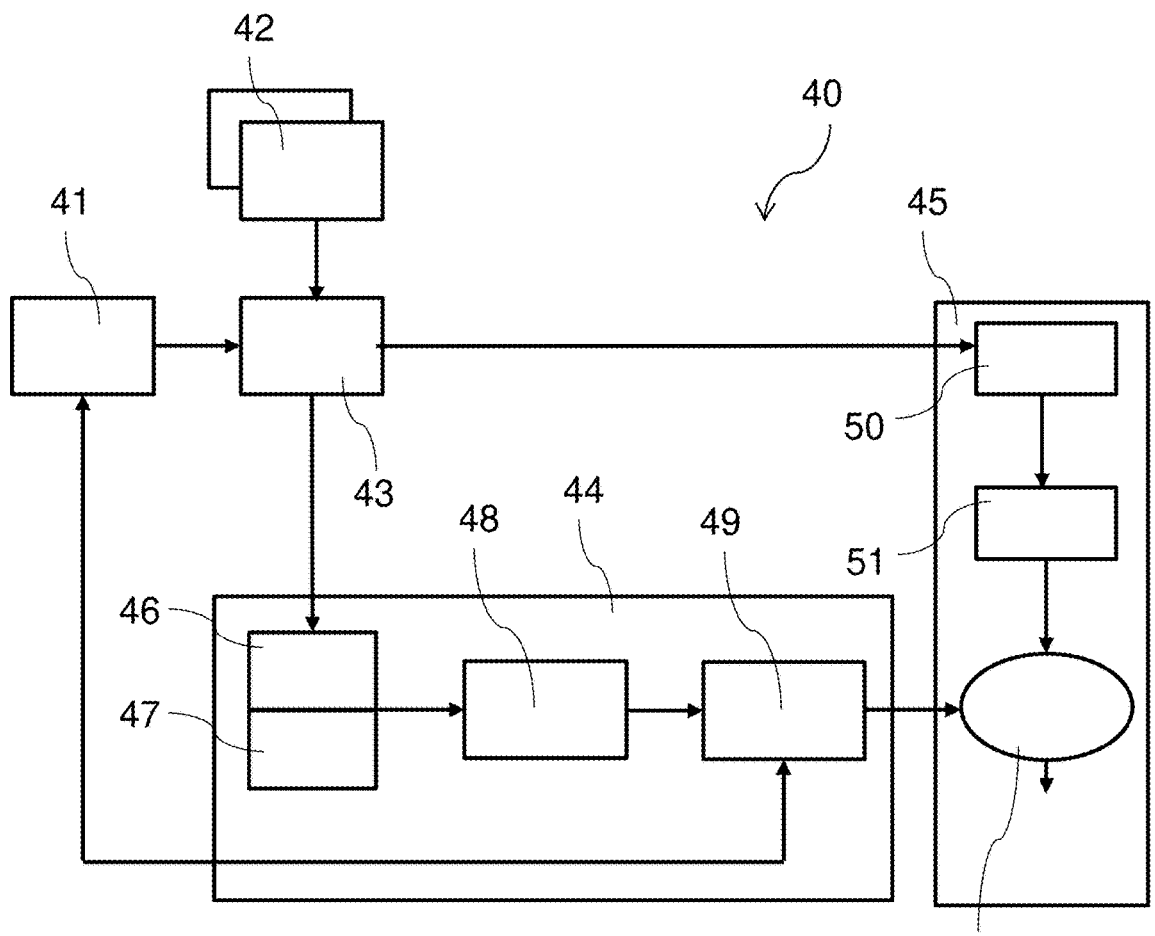
FIG. 2 represents, in the form of a block diagram, functions utilized for qualitatively evaluating liver grafts for liver transplants.

FIG. 2 shows means utilized in some embodiments 40 comprising training 44 and health evaluation 45. First of all, as shown in the left portion, training images 41 captured previously as described above are processed by an image processing means 43 which extracts at least one portion of the liver's image from each captured image 41. This portion of the liver's image is in turn processed to form at least one substantially uniform color sub-image (preferably, avoiding each image sub-portion representing a reflection, for example a saturation of at least one color, a shadow, for example at least one color being under a limit value by a few percent of the dynamics of the signal, a vein, a fissure, etc.). In FIG. 2, two sets, 46 and 47, each of eight image portions, are therefore produced. These sets 46 and 47 of sub-portions are chosen to cover as broadly as possible the different colors and/or the different textures of the extracted portion of the liver's image. In an equivalent way, or to achieve this objective, in some embodiments, the means 48 produces a histogram of colors and/or textures present (except for reflections or shadows of fissures) in the extracted liver image portion or another extraction of image characteristics, as described below. A specialist, for example a medical analysis laboratory performing biopsies, then gives an evaluation of the steatosis level. Possibly, a specialist, for example a surgeon, gives an opinion on the potential for transplanting the liver and/or lowering its fat with a view to its transplant and/or on the obesity treatment to be applied to the patient. Training defining a model 49 is then performed. This training can be performed statistically or with artificial intelligence.

During operation, a liver image 42 captured as described above follows the same image processing 43. Each image sub-portion 50 is sent to the device for evaluating the health of the liver. The extraction of characteristics 51 corresponds to the extraction of characteristics 48. On the basis of the model from the training 49, the means 52 for evaluating the steatosis level supplies a value of this level for the liver considered. Possibly, the evaluation means 52 automatically supplies an opinion on the potential for transplanting the liver and/or lowering its fat with a view to its transplant and/or on the obesity treatment to be applied to the patient.

In the embodiment shown in FIG. 2 for evaluating the HS by transplant, a dataset of sub-portions 100×100 in size is extracted from 40 RGB images of the livers of 40 different donors, of which half are livers accepted for transplant and half are rejected livers. A set of texture characteristics is computed from each sub-portion. These characteristics are used to form a classifier model. The model formed is used to evaluate the HS of transplant candidate livers.

With regard to the evaluation of the steatosis level as a function of the characteristics of the sub-portions of a liver image, its algorithm can be based on an analysis of texture based on training.

Particular embodiments, in particular applied to analyzing the health of candidate grafts, are described below.

These embodiments utilize an automatic analysis of the liver's texture using automatic training algorithms to automate the HS evaluation process and provide support to the surgeon's decision-making process.

For the training, at least forty RGB images of forty different donors are analyzed. The images are taken using a smartphone image capture device in the operating room. Half of the images concern livers that have been accepted and transplanted, and the other half concern liver grafts refused for transplant. Fifteen liver image sub-portions chosen at random have been extracted from each image, excluding the reflection areas and shadow areas. The size of the image sub-portion is, for example, 100×100 pixels. In this way, a balanced dataset of 600 correctives is obtained. The characteristics based on the intensity (INT), the histogram of the local binary model (HLBPriu2) and the greyscale co-occurrence matrix (FGLCM) are examined. The characteristics of the blood sample (Blo) have also been included in the analysis. The supervised and semi-supervised training approaches are analyzed for classifying characteristics.

With regard to the results with the best set of characteristics in this embodiment (HLBPriu2+INT+Blo) and the semi-supervised training, the sensitivity, uniqueness and precision of the classification are respectively 95%, 81% and 88%.

This automatic training and the automatic analysis of the textures of RGB images from smartphone image capture devices make it possible to evaluate the HS of grafts. The results show that it is an entirely automatic solution assisting surgeons to evaluate HS in an operating suite.

More details are given below about this algorithm example that can be used. Liver transplantation (one acronym of which is "LT") is the preferred treatment for patients suffering from late-stage liver disease, for which there are no other treatments. Because of the rise in demand and the shortage of organs, the expanded donor selection criteria are applied to increase the number of liver transplants. Given that the expanded criteria donors generate increased morbidity and mortality in the recipient population, evaluating the quality of liver grafts is crucial.

Analyzing the liver's texture has the advantage of being performed on a standard RGB image, without needing additional instrumentation. It should be noted that the cameras of modern cell phones provide high-quality images for evaluating the liver, and are ubiquitous.

The approach used in some embodiments for extracting and classifying textural entities is explained below. The strategy for extracting characteristics is explained ("Extraction of characteristics" section) and the training on the classification models ("Training on the models" section). The embodiments of the invention can in particular use the supervised ("Supervised approaches for classification by classes" section) and semi-supervised ("Supervised approaches for classifying images" section) classification approaches. The evaluation protocol, which includes the materials, parameterization and definition of performance measures, is explained in the "Evaluation" section.

It should be noted that the pathologist's biopsy classification is associated to the entire image, not to a single image sub-portion. Thus, the fact of considering all the sub-portions of an image of a graft having a high HS as pathological can influence the result of the classification, since the HS is not generally uniform in the liver tissue. Consequently, one preferably examines whether the MIL can support the HS diagnosis from sub-portions (unlabeled) extracted from RGB images (labeled). Among the MIL algorithms, one preferably uses single instance learning (SIL), which has the big advantage of allowing the amalgamation of range-based information (such as texture characteristics) with image-based information (such as the characteristics of blood samples), thus providing additional information for the classification process. For example, the popular SVM-SIL formula, which has shown good classification performance, is used.

The HS has been evaluated by means of histopathological analysis performed after a biopsy of the liver.

Figure 3:
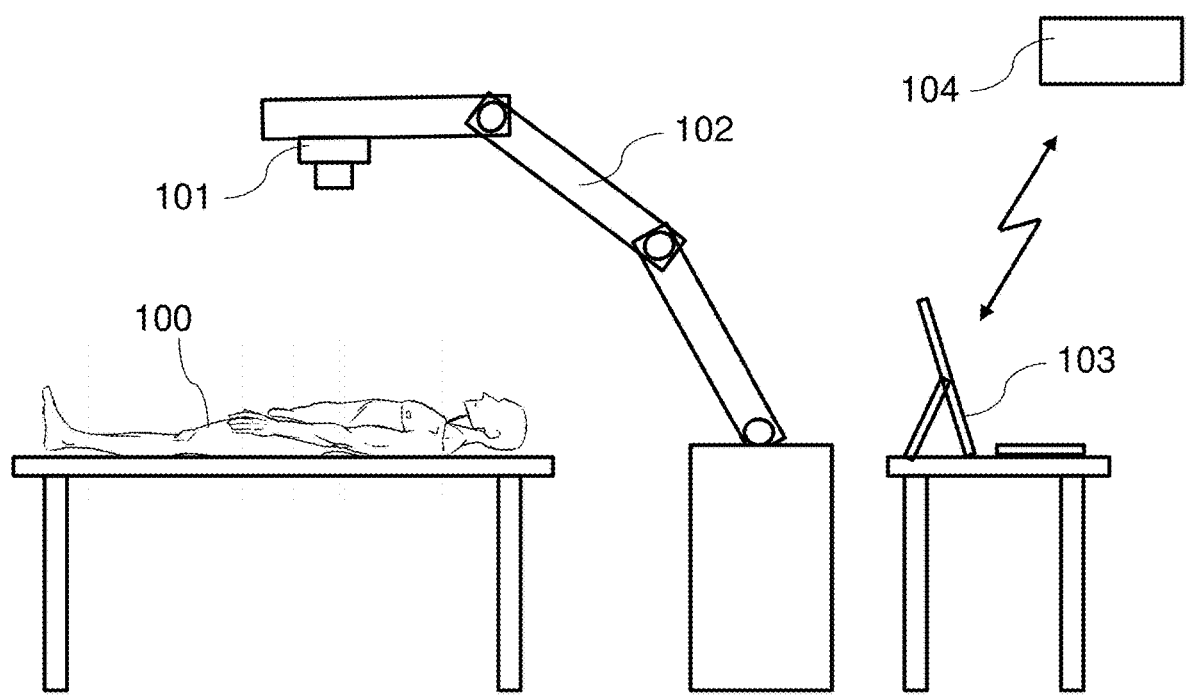
FIG. 3 represents, schematically, a particular embodiment of the device that is the subject of the invention.

FIG. 3 shows a patient or donor 100 positioned below an image capture means 101 supported by an articulated arm 102. A computer 103 receives images captured by the capture device 101 and performs the processing described above, possibly in collaboration with a remote server 104 that the computer 103 is in communication with.

Note that virtual reality glasses can be utilized to assist an operator or surgeon during the image capture and processing.

FIG. 4 shows the following series 110 of processing steps:
- a step 111 of inserting an image capture device, in particular a smartphone, in a sterile cover comprising a transparent window;
- a step 112 of opening an application and connecting to a server;
- a step 113 of image capture, for example using a flash source and possibly a color test chart for normalizing the image signal;
- a step 114 of extracting at least one portion of the liver's image, for example by manual, semi-automatic or automatic masking, preferably by eliminating the reflection areas and/or shadow areas;
- a step 115 of creating a directory for the patient or donor in question and inserting identification data and biological data into this directory;
- a step 116 of transmitting the extracted image to a remote server;
- a step 117 of segmenting the image into image sub-portions;
- a step 118 of classifying the set of image sub-portions for estimating a steatosis level;
- a step 119 of comparing the steatosis level with at least one predefined limit value to decide the treatment to be applied to livers, in particular, in the case of an envisaged transplant, decide whether the liver is transplantable as is, must have the fat lowered, or is not transplantable,
- a step 120 of receiving and storing results and possibly at least one image portion, in the directory of the patient or donor; and
- a step 121 of removal from the sterile cover.

An algorithm and a method for automatic liver segmentation by the acquisition of images is described below.

The goal is to present a deep learning solution for the segmentation of the graft using acquisition system images acquired in the operating suite.

The simulations were carried out on three hundred and thirty-four RGB images of different donors, and the Dice coefficient of similarity was 0.9668, the Recall was 0.9685 and the Precision was 0.9793. The proposed method envisages a fully automatic solution to assist the surgeon in the operating suite.

The approach based on analyzing the texture by means of a support-vector machine (SVM) to diagnose steatosis, working on RGB images obtained in the operating suite, was described above. This method, although it seems to have promising results, is limited in regard of the requirement for manual identification of the contour of the liver in the image.

The reference test for the identification of an organ's contours is manual segmentation, but it is not suitable since it depends on the operator and is unadaptable in a particular context such as the operating suite because of the requirement for the intervention of an operator. In addition, using large quantities of images can be a long and time-consuming process. One of the deep learning strategies involves certain convolutional filters that can hierarchically learn the characteristics of data. The role of the filters consists of extracting certain characteristics from input photos and collecting them in a map, which includes these functions. The number of filters for each kernel is chosen based on the time needed to train the network and the complexity of the problem. In general, a greater number of filters will give better results. This rule is only applied up to a certain threshold because, above this threshold, increasing the number of filters does not lead to better performance.

A method is presented below for automatically segmenting RGB images captured in the operating suite with the camera of a smartphone.

Figure 5:
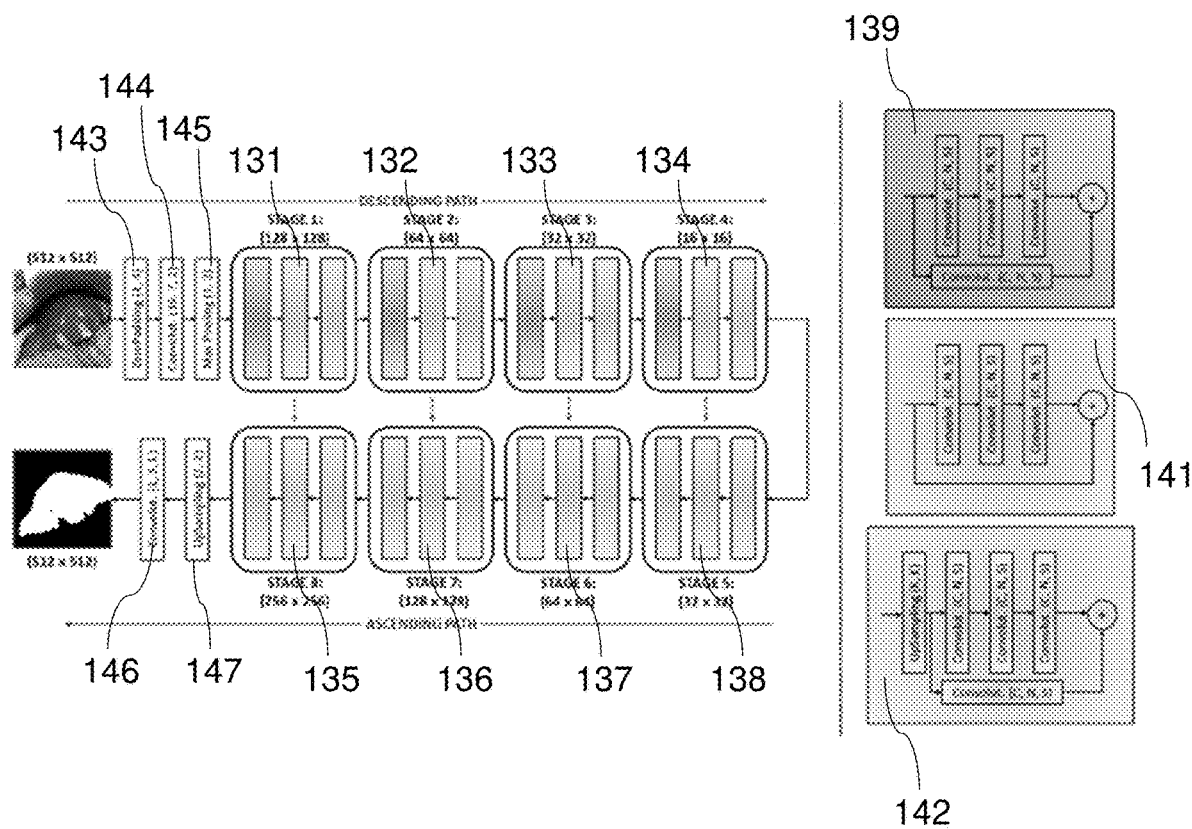
FIG. 5 is a diagram of a fully convolutional neural network.

In this study, a fully convolutional neural network ("FCNN") has been used. It consists of several kernels and layers, as shown in FIG. 5. In this case, the network model consists of a convolutional network (descending) and an ascending convolutional network. The convolutional neural path begins performing zero padding (4, 4) to add four rows and four columns above, below, on the left and on the right of the images table. Next, the FCNN continues with the convolutional neural path taken with sixteen (7×7) filters, followed by the normalization of batches, a rectified linear filter, activation of the unit (ReLU) and pooling (3, 3) with strides (2, 2). After these layers, the descending path continues with a convolutional block consisting of three successive convolutional filters and a shortcut connection with convolution 1×1. The convolutional block is followed by two convolutional identity blocks, consisting of three successive convolutional kernels and an identity shortcut connection. The combination of one convolutional block and two convolutional identity blocks is repeated four times (FIG. 5: step 131 to step 134). At each step, the number of convolutional filters per layer is doubled. The path of the ascending convolutional network is symmetrical to that of the descending convolution. Each step, repeated four times (in FIG. 5: step 135 to step 138), has a block for upscaling in the convolutional network. The ascending path ends with an upsampling block of size (2, 2) and a convolutional block, in this case with a filter (3×3) and a sigmoid type of activation.

FIG. 5 is a diagram of the fully convolutional neural network. On the left, the entire path can be split into two parts: the descending path (on the top) and the ascending path (on the bottom), each consisting of four steps. Each step of the descending path is made up of one convolutional block (boxes on the left) and two identification blocks (boxes in the center and on the right), whereas in the ascending path there is one upscaling block (boxes on the right) and two identification blocks (in the center and on the left).

The "ZeroPadding" block 143 represents a zero-padding layer (P, P), with padding P×P. The "Convolut." block 144 or 146 represents convolutional layer (C, N, S), with channels C, kernel size N×N and stride S. Each convolutional layer is followed by a layer of normalization by batches and a ReLU activation function. The "Max Pooling" block 145 indicates a maximum pooling operation (N, S) on N×N patches with stride S. The "UpSampling" function 147 indicates an upsampling operation (K×K) of size K. The vertical arrows in dashed lines indicate the concatenation of the map of characteristics from the descending convolution path to the ascending path. On the right, in 139, 141 and 142, an example of convolutional, identification and upscaling blocks is represented.

Figure 6:
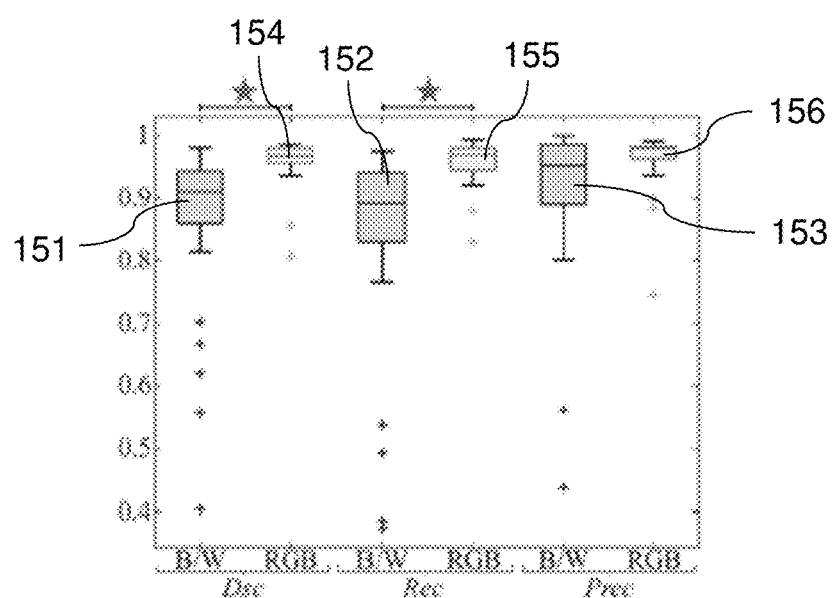
FIG. 6 represents a graph of similarity coefficients.

FIG. 6 is a Boxplot of the coefficients of Dice similarity (Dsc), Recall (Rec) and Precision (Prec) for the greyscale (boxplots 151 to 153) and RGB (boxplots 154 to 156) images. The stars indicate significant differences between the results obtained with RGB images and those with greyscale images.

With regard to the training (or learning), the Adam (adaptive momentum estimation) optimizer (registered trademark) has been used to train the FCNN network proposed. Adam estimated the first moment $\hat{m}_t$ and the second moment $\hat{v}_t$ of the gradient of the loss function to update a network parameter θ after t mini-batches:

$$\theta_t = \theta_{t-1} - \frac{\alpha}{\sqrt{\hat{v}_t(g_t)} + \epsilon} \cdot \hat{m}_t(g_t) \quad (1)$$

where α is the stride, gt is the gradient relative to the parameter θ after t mini-batches and ∈ is a small number. The cost function used in our simulation is the Dice similarity coefficient where TP is the number of true positives, FN the number of false negatives and FP the number of false positives. These terms are obtained from the pixels.

The following table shows the medians of the coefficients of Dice similarity (Dsc), recall (Rec) and Precision (Prec) obtained for the greyscale images and those for the RGB images. The interquartile ranges are indicated in brackets.

|  | Dsc | Rec | Prec |
|---|---|---|---|
| Greyscale | 0.9102 (0.0835) | 0.8919 (0.1104) | 0.9516 (0.0956) |
| RGB | 0.9668 (0.0234) | 0.9685 (0.0350) | 0.9793 (0.0191) |

$$Dsc = \frac{2 \times TP}{FN + FP + 2 \times TP} \quad (2)$$

Figure 7:
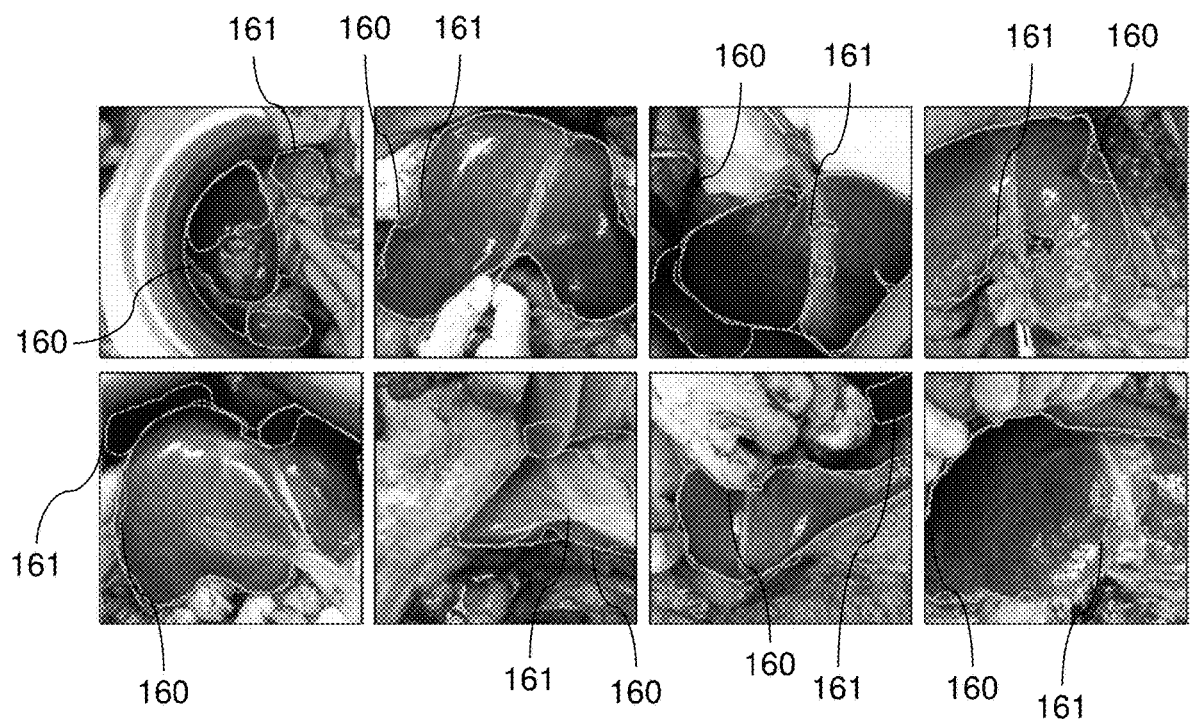
FIG. 7 represents examples of segmentation results, in the form of photographs.

FIG. 7 shows examples of segmentation results. Rows 161 and 160 refer respectively to the original greyscale mask and to the mask of the original RGB image.

The best analysis model for the validation Dsc was chosen, and was monitored during training. Two simulations were performed: in the first, the FCNN was trained with RGB photos, and in the second with greyscale images, obtained by converting the original photos. The main difference is in the pre-treatment phase and is linked to the dimensions of the photos where the images of the liver are recorded. In particular, they are differentiated by the number of channels.

With regard to the experimental protocol, three hundred and thirty-four RGB photos of different donors have been used. The size of the image was 1632*1224 pixels. The images were captured intraoperatively with a 12-megapixel RGB smartphone camera. For each image, a manual segmentation of the liver was performed to separate the liver from the background of the photo. In this way, the segmentation was obtained with manual tracing of the liver's contours.

The dataset for the training was made up of three hundred photos and three hundred corresponding manual liver masks. The (validation cohort) dataset consisted of thirty-four different images. We used RGB images in the first simulation whereas, in the second, the same images were converted into greyscale. For the first simulation, in the section relating to the preparation of the datasets, the pre-processing of the images and masks was performed to obtain a table of RGB images in which each image had three channels and a table of masks with one channel. Conversely for the second simulation the pre-processing was simpler and the greyscale images and masks were constructed as tables with a single channel.

In this section, the masks and the images were cropped to reduce their dimensions to 1224×1224 to make them square in shape. In succession, the images were successively resized to 512×512, to reduce the processing power and memory required, the proportions were maintained and the images were not deformed.

Next, we trained the FCNN, initially with a batch size of 15 over 100 iterations and a training rate of $10^{-2}$, then 100 other iterations with a batch of 15 and a lower training rate equal to $3 \times 10^{-5}$. A higher training rate was useful for accelerating the convergence since a lower value ensures that we have not missed the minimum performance levels required. 40% of the training images were used as a validation test.

The results of the automatic segmentation were compared to those of the manual segmentation, the gold standard. To evaluate the performance of the segmentation for the FCNN proposition, we computed the Dsc, Recall (Rec) and precision (Prec) of the predicted masks on MATLAB (registered trademark):

$$Rec = \frac{TP}{TP + FN}$$

$$Prec = \frac{TP}{TP + FP}$$

Where TP, FN and FP were already defined. For the training, the Wilcoxon rank-sum test (significance level equal to 5%) for medians, is used to evaluate whether there are statistical differences between the mask predicted from the RGB segmentation of the images and the greyscale segmentation of the images. All the experiments were performed on Google Colaboratory (registered trademarks). In contrast, the manual segmentations of the liver and statistical analysis were performed on MATLAB.

With regard to the results, a significant difference was found in comparing the Dsc and Rec computed for the predictive masks derived from the RGB images and the predictive masks derived from the greyscales. In contrast, no significant difference was discernible for the Prec. In particular, we deduced the Dsc, Rec and Prec interquartiles and the medians for the predicted masks from the simulation with RGB images outperforming the simulation with greyscales, as shown in the last table above. The results, shown in the boxplots in FIG. 6, were statistically validated with the Wilcoxon test. FIG. 7 shows a sample of the results from the segmentation where it is possible to compare the predictive masks, derived from the greyscales and RGB images with the manual masks.

In the last table, it is possible to see the results obtained with the automatic segmentation using the RGB images compared to the automatic segmentation using the greyscale images, in terms of Dsc, Rec and Prec. In particular, the Prec results show no significant difference, based on the Wilcoxon rank-sum (significance level a equal to 5%), as FIG.

6 shows. The Prec medians for the greyscale images and the RGB images are equal to 0.9516 and 0.9793 respectively. On the other hand, the Dsc and Rec results show significantly different results. The Dsc medians for the greyscale and RGB images are equal to 0.9102 and 0.9668 respectively. Conversely, the Rec medians for the greyscale images and the RGB images are equal to 0.8919 and 0.9685 respectively.

The use of greyscale images simplifies the model by improving from a clinical point of view, but the significant differences spotlighted by the statistical analysis suggest that better results can be obtained by using RGB images.

It can be seen that the worst predictions are obtained when the liver portion is small in the original image. Another aspect that might affect the predictions is the absence of a clear and sharp demarcation between the liver and the surrounding tissues. One example of poor liver mask prediction is shown by the sample in the upper left in FIG. 7.

What is claims is:

1. A device for qualitatively evaluating human livers, comprising:
    a camera for capturing an image of at least a portion of a liver, with the liver being in a donor's body, already removed, or placed in a hypothermic, normothermic and/or subnormothermic graft perfusion machine, when the image is captured;
    an image processor configured to select at least one portion of the captured image;
    a database including a set of image characteristics and liver variables, each characteristic is extracted from a training image of a liver and is associated with liver variables indicating health conditions of the liver shown on the training image;
    a classifier model trained to classify liver variables in accordance with image characteristics of liver images saved in the database; and,
    means for estimating the health of the liver, based on the selected portion of the captured image, said means for estimating is configured to extract image characteristics of said selected portion and to compare said image characteristics with corresponding image characteristics in said database using said classifier model, said means for estimating is further configured to assign a quality evaluation to the liver represented by the captured image, in accordance with classification of said image characteristics;
    wherein said means for estimating is further configured to calculate a predicted classification error in accordance with variables in said classification, and
    wherein the means for estimating is configured to compute a value representative of steatosis of the liver, said value being a linear combination of pixel numbers of color values, wherein said color values are components, of a histogram of the image, and wherein said pixel numbers are assigned multiplicator coefficients.

2. The device according to claim 1, wherein the image characteristics include pixel numbers extracted from the image corresponding to predefined color values forming components representative of the extracted image, to assign a quality evaluation to the liver represented by the captured image.

3. The device according to claim 1, wherein the means for estimating is configured to use, as principal components, a higher number of components for the values relating to the color red than for each of the colors blue or green.

4. The device according to claim 1, wherein the coefficients for the green color are, on average, negative and have a greater absolute value than for the other colors; the coefficients for the green color have a mean below mean of the coefficients for the other colors; and/or the coefficients for the blue color have a mean above the mean of the coefficients for the other colors.

5. The device according to claim 1, wherein most of the components correspond to color levels below a mean of the color levels in the histograms.

6. The device according to claim 1, wherein the number of components is less than one-fifth of the number of color levels.

7. The device according to claim 1, which comprises an estimator for estimating the sharpness of the captured image, separate from the camera for capturing an image of a liver.

8. The device according to claim 7, wherein the estimator for estimating the sharpness of the captured image is configured to utilize Sobel filtering.

9. The device according to claim 1, wherein said camera includes a lens and an optical widow fitted in front of the lens, said optical widow is configured to be inserted into the donor's body.

10. The device according to claim 1, wherein the image processor is configured to detect at least one reflection on the surface of the liver in the captured image, and to extract from the image at least one area presenting such a reflection.

11. The device according to claim 1, wherein the characteristics of said selected portion include a histogram of colors, wherein said means for estimating is configured to normalize said histogram.

12. The device according to claim 1, wherein the characteristics of said selected portion include textures of the liver.

13. The device according to claim 1, which also comprises a sterile cover configured to contain the camera and comprising a rigid transparent capturing window to be positioned in front of a lens unit of the camera.

14. The device according to claim 13, wherein the sterile cover comprises a polarizing filter to be positioned facing a light source, and a polarizing filter to be positioned facing the lens unit of the image capture means.

15. A method for qualitatively evaluating human livers, comprising:
    capturing an image of at least a portion of a liver, with the liver being in a donor's body, already removed, or placed in a hypothermic, normothermic and/or subnormothermic graft perfusion machine, when the image at least the liver is captured;
    selecting at least a portion of the captured image;
    means for estimating the health of the liver, based on the selected portion of the captured image, said means for estimating; is configured to extract image characteristics of said selected portion and to compare said image characteristics with corresponding image characteristics in said database, said means for estimating is further configured to assign a quality evaluation to the liver represented by the captured image, in accordance classification of said image characteristics;
    extracting image characteristics of said selected portion;
    comparing said image characteristics with corresponding image characteristics saved in a database including a set of image characteristics and liver variables, each characteristic is extracted from a training image of a liver and is associated with liver variables indicating health conditions of the liver shown on the training image;

training a classifier model trained to classify liver variables in accordance with image characteristics of liver images saved in the database;

assigning a quality evaluation to the liver represented by the captured image, in accordance classification of said image characteristics using said classifier model;

calculating a predicted classification error in accordance with variables in said classification, and computing a value representative of steatosis of the liver, said value being a linear combination of pixel numbers of color values, wherein said color values are components, of a histogram of the image, and wherein said pixel numbers are assigned multiplicator coefficients.

16. The method according to claim 15 further comprising:

a step of computing normalized histograms of color channels from a portion of a photograph of a liver;

a step of loading coefficients obtained at the end of a training phase;

a step of extracting from the histograms values corresponding to variables retained at the end of the training phase;

a step of computing a linear combination of the extracted values weighted with the loaded coefficients; and a step of displaying information representative of the result of the computation of the linear combination.

17. The method according to claim 16, which also comprises: a step of normalizing values of the reduced centered histograms, with the mean and standard deviation values from the training phase.

18. The method according to claim 16, wherein, during the display step, the computed result is displayed in an interval centered on the result and having a width equal to twice the standard deviation from the training phase.

* * * * *